US012751990B2

(12) United States Patent
Nangia et al.

(10) Patent No.: US 12,751,990 B2
(45) Date of Patent: Oct. 6, 2026

(54) METHOD OF TREATING A CHILD WITH CENTRAL PRECOCIOUS PUBERTY USING AN EXTENDED RELEASE COMPOSITION

(71) Applicant: Tolmar International Limited, Dublin (IE)

(72) Inventors: Avinash Nangia, Fort Collins, CO (US); John Arthur McLane, Loveland, CO (US)

(73) Assignee: Tolmar International Limited, Dublin (IE)

( * ) Notice: Subject to any disclaimer, the term of this patent is extended or adjusted under 35 U.S.C. 154(b) by 0 days.

(21) Appl. No.: 17/696,220

(22) Filed: Mar. 16, 2022

(65) Prior Publication Data

US 2022/0313772 A1 Oct. 6, 2022

Related U.S. Application Data

(63) Continuation of application No. 16/451,625, filed on Jun. 25, 2019, now abandoned.

(60) Provisional application No. 62/837,094, filed on Apr. 22, 2019.

(51) Int. Cl.
*A61K 38/09* (2006.01)
*A61K 9/00* (2006.01)
*A61K 47/22* (2006.01)
*A61K 47/34* (2017.01)
*A61M 5/19* (2006.01)
*A61P 15/00* (2006.01)

(52) U.S. Cl.
CPC ............ *A61K 38/09* (2013.01); *A61K 9/0019* (2013.01); *A61K 47/22* (2013.01); *A61K 47/34* (2013.01); *A61M 5/19* (2013.01); *A61P 15/00* (2018.01)

(58) Field of Classification Search
None
See application file for complete search history.

(56) References Cited

U.S. PATENT DOCUMENTS 6,565,874 B1 5/2003 Dunn et al.
6,773,714 B2 8/2004 Dunn et al.
8,470,359 B2 * 6/2013 Dunn .................... A61J 1/2089 424/443
8,486,455 B2 7/2013 Dunn et al.
8,840,916 B2 9/2014 Dunn
9,254,307 B2 2/2016 Dunn et al.
9,283,282 B2 * 3/2016 Dunn ................... A61K 9/0019
9,539,333 B2 1/2017 Dunn
9,914,802 B2 3/2018 Dunn
10,047,193 B2 8/2018 Dunn
2006/0019903 A1 * 1/2006 Kuzma ..................... A61P 5/02 514/11.1
2008/0194663 A1 8/2008 Dunn
2013/0288968 A1 * 10/2013 George ................... A61P 13/08 514/10.4
2014/0035757 A1 2/2014 Ramones et al.
2015/0150937 A1 * 6/2015 Dunn ....................... A61K 9/19 206/568
2015/0196485 A1 * 7/2015 Franco Rodriguez ....................... A61K 9/0024 514/383
2015/0297726 A1 * 10/2015 Yoon ................... A61K 9/0019 514/10.3
2016/0106805 A1 4/2016 Dunn et al.
2017/0096524 A1 4/2017 Dunn
2020/0039084 A1 2/2020 Duchaine et al.
2020/0330547 A1 10/2020 Nangia et al.
2022/0331523 A1 10/2022 Sherman et al.

OTHER PUBLICATIONS

Mayo Clinic Precocious puberty 2017.*
Partsch et al. “Management and outcome of central precocious puberty” 2002.*
Lee et al. “Morning basal leutinizing hormone, a good screening tool for diagnosing central precocious puberty” Mar. 2019.*
Prasad et al. “Evaluation of GnRH analogues in diagnosis and management of children with pubertal disorders” 2012.*
Carel “precocious puberty and structural growth” 2004.*
Carel et al. “Treatment of Central Precocious Puberty by Subcutaneous Injections of lueproelin 3-Month Depot (11.25 mg)” 2002.*
Klein et al. “Efficacy and safety of triptorelin 6-month formulation in patients with central precocious puberty” 2016.*
Kochar et al. “Leuprolide vs. triptorelin: The recent trends in GnRH analogues in precocious puberty” Feb. 2019.*
Ibanez et al. “Use of leuprolide acetate response patterns in the early diagnosis of pubertal disorders: comparison with the gonadotropin-releasing hormone test” (abstract) 1994.*
Carretto et al. “The Usefulness of the Leuprolide Stimulation Test as a Diagnosis Method of Idiopahic Central Precocious Puberty in Girls” 2014.*
Lee et al. “36-Month Treatment Experience of Two Doses of Leuprolide Acetate 3-Month Depot for Children with Central Precocious Puberty” 2014.*
FDA label for Triptodur Jun. 2017.*
FDA label Lupron Depot-Ped. Aug. 2011.*

(Continued)

*Primary Examiner* — Danah Al-Awadi
(74) *Attorney, Agent, or Firm* — Ballard Spahr LLP

(57) ABSTRACT

An extended release formulation is provided for use in a method for the treatment of Central Precocious Puberty (CPP) in pediatric patients 2 years of age or older. The extended release formulation comprises leuprolide or a pharmaceutically acceptable salt thereof, a biodegradable polymer, and a biocompatible organic solvent. The biodegradable polymer is comprised of poly(lactide-co-glycolide) (PLG) copolymer segments, poly(lactic acid-co-glycolic acid) (PLGA) copolymer segments, poly(lactide) (PL) polymer segments, poly(lactic acid) (PLA) polymer segments, or a combination thereof. The extended release formulation is administered as a subcutaneous injection of a flowable composition that forms a solid in situ depot. The extended release formulation releases leuprolide for a period of about 6 months for the effective treatment of CPP within a pediatric patient.

19 Claims, 7 Drawing Sheets

(56) References Cited

OTHER PUBLICATIONS

"A Study to Evaluate Safety, Efficacy, Pharmacokinetics, and Pharmacodynamics of Leuprolide Acetate 45mg 6-Month Formulation in Children With Central Precocious Puberty (CPP)," U.S. National Library of Medicine, last updated Jun. 18, 2019, NCT03695237, 7 pages [retrieved online from: clinicaltrials.gov/ct2/show/NCT03695237?term=lupron+depot&cond=Central+Precocious+Puberty&draw=2&rank=2].
"Comparative Validation of the Triptorelin Test for the Diagnosis of CPP in Girls," U.S. National Library of Medicine, last updated Jan. 17, 2011, NCT01278290, 5 pages [retrieved online from: clinicaltrials.gov/ct2/show/NCT01278290].
"E11(R1) Addendum: Clinical Investigation of Medicinal Products in the Pediatric Population Guidance for Industry," U.S. Department of Health and Human Services Food and Drug Administration, Apr. 2018, 14 pages.
"Guideline on pharmaceutical development of medicines for paediatric use," European Medicines Agency, Aug. 2013, EMA/CHMP/QWP/805880/2012 Rev. 2, 24 pages.
"Lupron Depot-Ped (leuprolide acetate for depot suspension) FDA Label," FDA, May 2017, 22 pages.
"Lupron Depot (leuprolide acetate for depot suspension) FDA Label," FDA, Jul. 2014, 31 pages.
"Precocious puberty," Mayo Clinic, 2017, 6 pages.
"Supprelin La (histrelin acetate) FDA Label," FDA, May 2017, 20 pages.
"Triptodur (triptorelin) FDA Label," FDA, Jun. 2017, 13 pages.
Antoniazzi et al. "Central Precocious Puberty: Current Treatment Options," Pediatric Drugs, Jul. 2004, vol. 6, No. 4, pp. 211-231.
Badaru et al. "Sequential Comparisons of One-Month and Three-Month Depot Leuprolide Regimens in Central Precocious Puberty," The Journal of Clinical Endocrinology & Metabolism, 2006, vol. 91, No. 5, pp. 1862-1867.
Carel et al. "Treatment of Central Precocious Puberty by Subcutaneous Injections of Leuprorelin 3-Month Depot (11.25 mg)," The Journal of Clinical Endocrinology & Metabolism, 2002, vol. 87, No. 9, pp. 4111-4116.
Carel et al. "Precocious Puberty," The New England Journal of Medicine, May 2008, vol. 358, No. 22, pp. 2366-2377.
Carel "Precocious puberty and statural growth," Human Reproduction Update, 2004, vol. 10, No. 2, pp. 135-147.
Carretto et al. "The Usefulness of the Leuprolide Stimulation Test as a Diagnostic Method of Idiopathic Central Precocious Puberty in Girls," Hormone and Metabolic Research, 2014, vol. 46, No. 13, pp. 959-963.
Freire et al. "High diagnostic accuracy of subcutaneous Triptorelin test compared with GnRH test for diagnosing central precocious puberty in girls," Clinical Endocrinology, 2013, vol. 78, pp. 398-404.
Fuld et al. "A Randomized Trial of 1- and 3-Month Depot Leuprolide Doses in the Treatment of Central Precocious Puberty," The Journal of Pediatrics, Dec. 2011, vol. 159, No. 6, pp. 982-987.
Fuqua "Treatment and Outcomes of Precocious Puberty: An Update," The Journal of Clinical Endocrinology & Metabolism, Jun. 2013, vol. 98, No. 6, pp. 2198-2207.
Ghai et al. "Gonadotropin Releasing Hormone Agonist (Nafarelin) Test to Differentiate Gonadotropin Deficiency from Constitutionally Delayed Puberty in Teen-age Boys—A Clinical Research Center Study," Journal of Clinical Endocrinology and Metabolism, 1995, vol. 80, No. 10, pp. 2980-2986.
Houk et al. "The Diagnostic Value of a Brief GnRH Analogue Stimulation Test in Girls with Central Precocious Puberty: A Single 30-minute Post-stimulation LH Sample is Adequate," Journal of Pediatric Endocrinology & Metabolism, 2008, vol. 21, No. 12, pp. 1113-1118.
Ibanez et al. "Use of leuprolide acetate response patterns in the early diagnosis of pubertal disorders: comparison with the gonadotropin-releasing hormone test." The Journal of Clinical Endocrinology and Metabolism, Jan. 1994, vol. 78, No. 1, pp. 30-35 (abstract).
Kim et al. "Multicenter clinical trial of leuprolide acetate depot (Luphere depot 3.75 mg) for efficacy and safety in girls with central precocious puberty," Annals of Pediatric Endocrinology & Metabolism, Dec 2013, vol. 18, No. 4, pp. 173-178.
Lee et al. "Morning basal luteinizing hormone, a good screening tool for diagnosing central precocious puberty," Annals of Pediatric Endocrinology & Metabolism, Mar. 2019, vol. 24, No. 1, pp. 27-33.
Mahmood "Dosing in Children: A Critical Review of the Pharmacokinetic Allometric Scaling and Modelling Approaches in Paediatric Drug Development and Clinical Settings," Clinical Pharmacokinetics, 2014, vol. 53, pp. 327-346.
Menon "Precocious Puberty, GnRH Stimulation Test and Monitoring GnRH Analog Therapy," The Indian Journal of Pediatrics, Nov. 2015, vol. 82, No. 11, pp. 980-982.
Neely et al. "Leuprolide Acetate 1-Month Depot for Central Precocious Puberty: Hormonal Suppression and Recovery," International Journal of Pediatric Endocrinology, 2010, 398639, 16 pages.
O'Hara "Paediatric pharmacokinetics and drug doses," Australian Prescriber, Dec 2016, vol. 39, No. 6, pp. 208-210.
Okada "One- and three-month release injectable microspheres of the LH-RH superagonist leuprorelin acetate," Advanced Drug Delivery Reviews, Jan. 1997, vol. 28, pp. 43-70.
Park et al. "Comparative in vitro release and clinical pharmacokinetics of leuprolide from Luphere 3M Depot, a 3-month release formulation of leuprolide acetate," Drug Development and Industrial Pharmacy, Mar. 2017, vol. 43, No. 3, pp. 441-447.
Partsch et al. Management and outcome of central precocious puberty, Clinical Endocrinology, 2002, vol. 56, pp. 129-148.
Prasad et al. Evaluation of GnRH analogue testing in diagnosis and management of children with pubertal disorders, Indian Journal of Endocrinology and Metabolism, May-Jun. 2012, vol. 16, No. 3, pp. 400-405.
Ravivarapu et al. "Sustained Suppression of Pituitary-Gonadal Axis with an Injectable, In Situ Forming Implant of Leuprolide Acetate," Journal of Pharmaceutical Sciences, Jun. 2000, vol. 89, No. 6, pp. 732-741.
Wilson et al. "Evaluation of the Buserelin Stimulation Test in Diagnosing Gonadotropin Deficiency in Males with Delayed Puberty," The Journal of Pediatrics, Jan. 2006, vol. 148, No. 1, pp. 89-94.
Witchel et al. "Treatment of Central Precocious Puberty: Comparison of Urinary Gonadotropin Excretion and Gonadotropin-Releasing Hormone (GnRH) Stimulation Tests in Monitoring GnRH Analog Therapy," Journal of Clinical Endocrinology and Metabolism, 1996, vol. 81, No. 4, pp. 1353-1356.
International Search Report and Written Opinion for International (PCT) Patent Application No. PCT/IB2020/053767, dated Jul. 30, 2020 16 pages.
Official Action for U.S. Appl. No. 16/451,625, dated Sep. 20, 2019 20 pages.
Official Action for U.S. Appl. No. 16/451,625, dated Jan. 10, 2020 28 pages.
Official Action for U.S. Appl. No. 16/451,625, dated Jun. 12, 2020 24 pages.
Official Action for U.S. Appl. No. 16/451,625, dated May 13, 2021 26 pages.
Examiner's Answer for U.S. Appl. No. 16/451,625, dated Nov. 15, 2021 30 pages.
Decision on Appeal for U.S. Appl. No. 16/451,625, dated May 6, 2022 34 pages.
Lee et al., "36-Month Treatment Experience of Two Doses of Leuprolide Acetate 3-Month Depot for Children With Central Precocious Puberty," Journal of Clinical Endocrinology and Metabolism, vol. 99, No. 9, Sep. 2014, pp. 3153-3159.
Oerter et al., "Gonadotropin Secretory Dynamics During Puberty in Normal Girls and Boys," Journal of Clinical Endocrinology and Metabolism, vol. 71, No. 5, Nov. 1990, pp. 1251-1258.
U.S. Federal Drug Administration (FDA)—Package insert, Drug approval for Eligard, Accessed from:https://www.accessdata.fda.

(56) References Cited

OTHER PUBLICATIONS gov/drugsatfda_docs/nda/2004/021731s000_Eligard_PRNTLBL.pdf.

* cited by examiner

METHOD OF TREATING A CHILD WITH CENTRAL PRECOCIOUS PUBERTY USING AN EXTENDED RELEASE COMPOSITION

CROSS-REFERENCE TO RELATED APPLICATIONS

This application is a continuation of U.S. patent application Ser. No. 16/451,625, filed 25 Jun. 2019, now abandoned, which claimed the benefit of U.S. Provisional Patent Application 62/837,094, filed 22 Apr. 2019, the entireties of which are incorporated herein by reference, for all purposes.

FIELD OF THE INVENTION

This application pertains to the field of treating central precocious puberty (CPP) in children of at least 2 years of age using biodegradable polymer compositions that may be administered into the body with syringes or needles for the delivery of a GnRH agonist into the body over an extended period of time.

BACKGROUND OF THE INVENTION

Precocious Puberty (PP) is characterized by early onset of pubertal changes to a child of at least 2 years of age. PP is further divided into two classifications: Peripheral Precocious Puberty (PPP) or Central Precocious Puberty (CPP) (Fuqua J S. "Treatment and outcomes of precocious puberty: an update". J Clin Endocrinol. Metab. 2013; 98(6): 2198-2207). PPP is defined by early sexual development prompted by sex steroids resulting from abnormal endogenous or exogenous sources such as disease or environmental exposure. PPP associated symptoms, such as ambiguous genital development or virilization in females, can result from insufficient androgen levels caused by various tumors (i.e. gonadal, adrenal, germ cell tumors, etc.). Conversely, CPP is defined by early sexual development prompted by production and release of gonadotropins and/or sex steroids from normal endogenous sources including the hypothalamus or pituitary. Identification of CPP can be made by use of a stimulation test (Carretto, F., et al. "The usefulness of the leuprolide stimulation test as a diagnostic method of idiopathic central precocious puberty in girls". Horm Metab Res. 2014; 46(13): 959-963). Aberrations in gonadotropin and/or sex hormone concentration levels in children with CPP can result from various sources, including, but not limited to, physical injury, infection, genetic disease, or associated tumors. CPP caused by a genetic or undetermined pathology is classified to be idiopathic in nature, while CPP caused by a central nervous system (CNS) tumor and/or lesion is classified as organic in nature. CPP is accompanied by advanced bone age, accelerated growth velocity, and Hypothalamic-Pituitary-Gonadal-axis activation. Idiopathic CPP is more prevalent in female children, whereas males more commonly display distinguishable organic CPP pathologies.

Idiopathic CPP and organic CPP can both be treated using gonadotropin releasing hormone (GnRHa) therapy (Antoniazzi, F., "Central precocious puberty: current treatment options". Paediatr. Drugs. 2004; 6(4): 211-231). Current methods of treating a child with CPP rely upon administration of GnRH or GnRH agonists. Sustained delivery of GnRH or GnRH agonists results in chronic stimulation of GnRH receptors in the pituitary, which after an initial transient increase, leads to subsequent to downregulation of GnRH receptor activity. Downregulation of GnRH receptor activity reduces GnRH-dependent secretion of gonadotropins, including but not limited to luteinizing hormone (LH) and follicle-stimulating hormone (FSH), which are key drivers of normal development during puberty. Reduction in gonadotropin secretion, also known as hypogonadism, consequently helps to slow and potentially reverse the early onset of pubertal changes and symptoms associated with CPP. Conversely, GnRH and GnRH agonists are not used in treatment of PPP Instead, PPP treatment options include, but are not limited to, use of P450 inhibitors, antiandrogens, aromatase inhibitors, and estrogen receptor inhibitors.

Despite the availability of GnRH-based treatments for CPP, limitations in current treatment options emphasize the continuous need for novel compositions with desirable extended release properties for the prolonged release of GnRH or GnRH agonists for treating CPP in children of at least 2 years of age. Approved and marketed extended release products based on using GnRH agonists for the treatment of CPP in children include, but are not limited to: 1) LUPRON DEPOT-PED®, a 1 or 3 month leuprolide acetate-based microsphere formulation administered intramuscularly in a 1.0 or 1.5 mL volume, with varying and adjustable dosage (7.5, 11.25, or 15 mg for 1 month; 11.25 or 30 mg for 3 month) based upon the child's weight and/or the child's clinical response to the formulation; 2) TRIPTODUR®, a fixed dose (22.5 mg), 6 month triptorelin acetate-based microgranule formulation administered intramuscularly in a 2 mL volume; and 3) SUPPRELIN LA®, a fixed dose (50 mg), 12 month histrelin acetate-based, non-biodegradable, hydrogel polymer reservoir that is implanted subcutaneously.

However, all currently approved and marketed treatments for CPP in children have limitations and disadvantages, such as difficulty of formulation preparation and administration, inconsistent dosing issues, inadequate/inconvenient effective period (i.e., the interval between doses is too short), patient discomfort, patient non-compliance, patient-to-patient variability, and difficult removal/disposal of the formulation if discontinuation of treatment is desired. For instance, both LUPRON DEPOT-PED® and TRIPTODUR® are composed of polymer-based microspheres or microgranules, which have costly and complex manufacturing requirements. Furthermore, microspheres are known to settle out of solution over time. Therefore, microsphere based formulations, such as LUPRON DEPOT-PED® and TRIPTODUR™, must be properly prepared and administered by a physician to ensure correct dosing is achieved and maintained. Both LUPRON DEPOT-PED® and TRIPTODUR® are administered as large volume doses (i.e., up to 2 mL per dose) to children via deep, intramuscular injection. Such injections can be exceedingly painful and difficult to perform, especially for smaller and more easily frightened children. Similarly, SUPPRELIN LA® is administered as a non-biodegradable implant, which must be surgically inserted into the inner aspect of the upper arm using a cannula, typically under local or general anesthesia or sedation; removal of the implant requires a similar surgical procedure. Additionally, LUPRON DEPOT-PED® requires the administered dose to be continuously individualized and adjusted based upon the weight of the child and/or the sufficiency of the child's clinical response to the therapy throughout the course of treatment.

While, LUPRON DEPOT-PED®, TRIPTODUR™, and SUPPRELIN LA® provide continuous release of a GnRH agonist for 1, 3, 6, and 12 months, respectively, there is a critical need to balance patient compliance and comfort, which is especially difficult in children as young as 2 years of age, with effective and convenient treatment. Treatment of CPP in a child of at least 2 years of age may need to persist for years, and as such, requires numerous doctor visits. Therefore, there is a need in the art for an effective, more tolerable treatment that comprises the extended release of GnRH or a GnRH agonist over a clinically useful time period that minimizes repeated administrations and adjustment of dosage based on body weight, while also minimizing the difficulty, pain, and bleeding associated with said administration. Such a therapy would be highly advantageous over current CPP treatment options.

SUMMARY OF INVENTION

The present invention provides methods of treating a child (also referred to herein as a pediatric patient) of at least 2 years of age with central precocious puberty (CPP) by administering a subcutaneous injection of an extended release composition comprising a biodegradable polymer capable of providing for the extended release of a GnRH agonist medicament in vivo when injected once per six months. The extended release formulation comprising the biodegradable polymer further comprises a GnRH agonist, such as leuprolide or a pharmaceutically acceptable salt thereof, for the treatment of CPP. The present invention also provides methods of using an optional stimulation composition in combination with the extended release composition for the treatment of CPP within a child of at least 2 years of age. The stimulation composition comprises GnRH or a GnRH agonist, or a pharmaceutically acceptable salt thereof, and is administered subcutaneously to the child for measuring peak stimulated blood serum LH concentration within the child. Lastly, the present invention also provides for a kit containing the extended release composition and stimulation composition for the treatment of a child with CPP.

In one embodiment of the invention, a child of at least two years of age who has CPP is administered a subcutaneous injection of an extended release composition once per about six months. The extended release composition comprises an organic solvent, leuprolide or a pharmaceutically acceptable salt thereof, and a biodegradable polymer. The amount of leuprolide or the pharmaceutically acceptable salt thereof in the extended release composition is independent from the weight of the child and is not modified in subsequent administrations of the composition. The biodegradable polymer comprises polymer segments selected from 85:15 poly (lactide-co-glycolide) (PLG) copolymer segments, 85:15 poly(lactic acid-co-glycolic acid) (PLGA) copolymer segments, poly(lactide) (PL) polymer segments, poly(lactic acid) (PLA) polymer segments, or a combination thereof. The biodegradable polymer has substantially no titratable carboxylic acid groups and at least one distal end group of the polymer is hydroxyl-terminated. Upon contact with a bodily fluid, the organic solvent in the extended release composition dissipates, such that an in situ solid depot forms. When administered to a child with CPP once per about six months, the extended release composition reduces the child's peak stimulated blood serum LH concentration to a pre-pubertal concentration level of <4 IU/L.

In another embodiment of the invention, a pediatric patient two years of age and older who has CPP is administered a subcutaneous injection of an extended release composition once per about six months. The extended release composition comprises an organic solvent, leuprolide or a pharmaceutically acceptable salt thereof, and a biodegradable polymer. The amount of leuprolide or the pharmaceutically acceptable salt thereof in the extended release composition is independent from the weight of the pediatric patient and is not modified in subsequent administrations of the composition. The biodegradable polymer comprises polymer segments selected from 85:15 poly(lactide-co-glycolide) (PLG) copolymer segments, 85:15 poly (lactic acid-co-glycolic acid) (PLGA) copolymer segments, or a combination thereof. The biodegradable polymer has substantially no titratable carboxylic acid groups and at least one distal end group of the polymer is hydroxyl-terminated. Upon contact with a bodily fluid, the organic solvent in the extended release composition dissipates, such that an in situ solid depot forms. When administered to a pediatric patient with CPP once per about six months, the extended release composition reduces the pediatric patient's peak stimulated blood serum LH concentration to a pre-pubertal concentration level of <4 IU/L. In some embodiments, the organic solvent is N-methyl-2-pyrrolidone (NMP).

In another embodiment of the invention, a child of at least two years of age who has CPP is administered a subcutaneous injection of an extended release composition comprising an organic solvent, leuprolide or a pharmaceutically acceptable salt thereof, and a biodegradable polymer. The amount of leuprolide or the pharmaceutically acceptable salt thereof in the extended release composition is independent from the weight of the child and is not modified in subsequent administrations of the composition. The biodegradable polymer comprises polymer segments selected from 85:15 poly(lactide-co-glycolide) (PLG) copolymer segments, 85:15 poly(lactic acid-co-glycolic acid) (PLGA) copolymer segments, poly(lactide) (PL) polymer segments, poly(lactic acid) (PLA) polymer segments, or a combination thereof. The biodegradable polymer has substantially no titratable carboxylic acid groups and at least one distal end group of the polymer is hydroxyl-terminated. At least once at about three to six months after administering the extended release composition, the child is administered a subcutaneous injection of a stimulation composition comprising GnRH or a GnRH agonist, or a pharmaceutically acceptable salt thereof, to confirm suppression of peak blood serum LH concentration to pre-pubertal level of <4 IU/L within the child. If the peak stimulated blood serum LH concentration at about three to about six months after administering the extended release composition is <4 IU/L, then additional administrations of the extended release composition and stimulation composition may be repeated as necessary to continue treatment of CPP within the child. Upon contact with a bodily fluid, the organic solvent in the extended release composition dissipates, such that an in situ solid depot forms. When administered to a child with CPP once per about six months, the extended release composition reduces the child's peak stimulated blood serum LH concentration to a pre-pubertal concentration level of <4 IU/L.

In another embodiment of the invention, pediatric patients two years of age or older who have CPP are administered a subcutaneous injection of a stimulation composition for measuring the peak stimulated blood serum LH concentration from a blood sample obtained from the pediatric patient within about at least thirty minutes of administering the stimulation composition. The stimulation composition comprises GnRH or a GnRH agonist, or a pharmaceutically acceptable salt thereof. The pediatric patient is then administered a subcutaneous injection dose of an extended release composition effective for treating CPP for about six months if the pediatric patient has a peak stimulated blood serum LH concentration of >5 IU/L. The dose of the extended release composition is not individualized for the pediatric patient. The drug product also allows for injection at any site with an adequate amount of subcutaneous tissue. The extended release composition comprises the organic solvent N-methyl-2-pyrrolidone (NMP), leuprolide or a pharmaceutically acceptable salt thereof, and a biodegradable polymer. The biodegradable polymer comprises polymer segments selected from 85:15 poly(lactide-co-glycolide) (PLG) copolymer segments, 85:15 poly(lactic acid-co-glycolic acid) (PLGA) copolymer segments, poly(lactide) (PL) polymer segments, poly(lactic acid) (PLA) polymer segments, or a combination thereof. The biodegradable polymer has substantially no titratable carboxylic acid groups and at least one distal end group of the polymer is hydroxyl-terminated. At about three to six months after administering the extended release composition, the pediatric patient is administered an additional injection of the stimulation composition to confirm suppression of peak stimulated blood serum LH concentration to a pre-pubertal level of <4 IU/L from a blood serum sample obtained from the pediatric patient within about at least thirty minutes of administering the additional stimulation composition for measuring a peak stimulated blood serum LH concentration. If the peak stimulated blood serum LH concentration at about three to about six months after administering the extended release composition is <4 IU/L, then additional administrations of the extended release composition and stimulation composition may be repeated as necessary to continue treatment of CPP within the pediatric patient. The dose of the extended release composition is not individualized for the pediatric patient and upon contact with a bodily fluid, the organic solvent in the extended release composition dissipates such that an in situ solid depot forms. When administered to a pediatric patient with CPP once per about six months, the extended release composition reduces the child's peak stimulated blood serum LH concentration to a pre-pubertal concentration level of <4 IU/L.

In some embodiments, the amount of leuprolide or the pharmaceutically acceptable salt thereof in the extended release composition is about 40 mg to about 50 mg. In other embodiments, the leuprolide or the pharmaceutically acceptable salt thereof is leuprolide acetate in an amount of about 45 mg.

In some embodiments, the amount of leuprolide or the pharmaceutically acceptable salt thereof in the extended release composition is about 40 mg to 45 mg leuprolide free base equivalent. In other embodiments, the amount of leuprolide or the pharmaceutically acceptable salt thereof in the extended release composition is about 42 mg leuprolide free base equivalent.

In some embodiments, a stimulation composition comprising GnRH or a GnRH agonist, or a pharmaceutically acceptable salt thereof, is administered subcutaneously to the child for measuring peak stimulated blood serum LH concentration within the child prior to administration of the extended release composition. In some embodiments, a stimulation composition comprising GnRH or a GnRH agonist, or a pharmaceutically acceptable salt thereof, is administered subcutaneously to the pediatric patient for measuring peak stimulated blood serum LH concentration within the pediatric patient prior to administration of the extended release composition to confirm a baseline peak stimulated blood serum LH concentration. In some embodiments, a stimulation composition comprising GnRH or a GnRH agonist, or a pharmaceutically acceptable salt thereof, is administered subcutaneously to the pediatric patient for measuring peak stimulated blood serum LH concentration within the pediatric patient at about three to about six months after administration of the extended release composition to confirm suppression of peak stimulated blood serum LH concentration to a pre-pubertal level of <4 IU/L. In some embodiments, a blood sample from the child is obtained within about at least thirty minutes of administering the stimulation composition(s) for measuring the peak stimulated blood serum LH concentration(s).

In some embodiments, the stimulation composition may comprise at least one GnRH agonist or pharmaceutically salt thereof selected from a group consisting of leuprolide, gonadorelin, goserelin, histrelin, nafarelin, buserelin, and triptorelin. In some embodiments, the stimulation composition may comprise a GnRH solution administered, generally by subcutaneous injection, at a dose of either: 1) about 2.5 μg per kg of the child's body weight or 2) about 100 μg total. In some embodiments, the stimulation composition may comprise a leuprolide acetate solution administered subcutaneously at a dose of either: 1) about 10 μg to about 20 μg per kg of the child's or pediatric patient's body weight or 2) about 500 μg to about 1000 μg total. In some embodiments, the stimulation composition may comprise a nafarelin acetate solution administered subcutaneously at a dose of either: 1) about 1 μg per kg of the child's body weight or 2) about 100 μg total. In some embodiments, the stimulation composition may comprise a buserelin solution administered subcutaneously at a dose of about 100 μg total. In some embodiments, the stimulation composition may comprise a triptorelin acetate solution administered subcutaneously at a dose of about 100 μg total.

In some embodiments, the peak stimulated blood serum concentration levels of one or more additional CPP-associated hormones selected from the group consisting of follicle stimulating hormone (FSH), testosterone, and estradiol, may be measured from within the blood samples obtained from the child or pediatric patient following administration of the stimulation composition. In some embodiments, administration of the extended release composition may reduce peak stimulated blood serum FSH to a concentration of ≥2.5 IU/L. In some embodiments, administration of the extended release composition may reduce peak stimulated blood serum estradiol in a female child to a concentration of <73.4 pmol/L (<20 pg/mL). In some embodiments, administration of the extended release composition may reduce peak stimulated blood serum estradiol in a female pediatric patient to a concentration of <73.4 pmol/L (<20 pg/mL). In some embodiments, administration of the extended release composition may reduce peak stimulated blood serum testosterone in a male child to a concentration of <1 nmol/L (<28.8 ng/dL). In some embodiments, administration of the extended release composition may reduce peak stimulated blood serum testosterone in a male pediatric patient to a concentration of <1 nmol/L (<28.8 ng/dL).

In some embodiments, a dose of the extended release composition may comprise: 1) about 165 mg of N-methyl-2-pyrrolidone (NMP), 2) about 165 mg of about 85:15 poly(DL lactide-co-glycolide) (PLG) copolymer segments, and 3) about 45 mg of leuprolide acetate.

In some embodiments, the biodegradable polymer of the extended release composition may have a weight average molecular weight of between 15 kDa to 45 kDa, preferably 20 kDa to 26 kDa.

In some embodiments, the biodegradable polymer of the extended release composition may comprise a polymer of the Formula: HO—(P)—C(═O)O—Ra-O(O═)C—(P)—OH, wherein, Ra is an alkane diradical comprising about 4 to about 8 carbons and is a residue of an alkane diol and wherein P are the polymeric segments.

In some embodiments, the extended release composition may reduce the mean growth velocity in a child or pediatric patient with CPP by about 25% over about a twelve-month treatment period. In some embodiments, administration of the extended release composition may reduce the child's mean ratio of bone age to chronological age at the time of measurement by about 3% at about six months and about 5% at the end of treatment (at about twelve months). In some embodiments, administration of the extended release composition may reduce the pediatric patient's mean ratio of bone age to chronological age at the time of measurement by about 5% over about a twelve-month treatment period.

In some embodiments, the extended release composition comprises an injection dose volume of about 0.5 mL or less. In some instances, the extended release composition comprises an injection dose volume of about 0.375 mL.

In some embodiments, the pediatric patient with CPP is treated with the extended release composition for a time period of about 6 months, of about 12 months, of about 18 months, of about 24 months, or longer.

In some embodiments, the extended release composition is provided in a two-syringe system comprising a first syringe containing about 45 mg of lyophilized leuprolide acetate or an equivalent amount of a different pharmaceutically acceptable salt of leuprolide and a second syringe containing a solution of about 165 mg of about 85:15 poly(lactide-co-glycolide) (PLG) copolymer segment dissolved in about 165 mg of N-methyl-2-pyrrolidone (NMP). The first syringe is connected to the second syringe such that a passageway is formed between the first syringe and the second syringe to allow the passage of a flowable composition from one syringe to the other syringe. The extended release composition is prepared by continuously mixing the contents of the second syringe back and forth into the contents of the first syringe of the connected two-syringe system for at least about 45 seconds to about at least 60 seconds or longer to form a uniform suspension.

In some embodiments, the invention provides a method of treating a pediatric patient 2 years of age and older with CPP, by firstly administering an injection of a stimulation composition comprising GnRH or a GnRH agonist, or a pharmaceutically acceptable salt thereof, to the pediatric patient 2 years of age or older who has CPP, wherein a blood sample from the pediatric patient is obtained within about at least thirty minutes of administering the stimulation composition for measuring a peak stimulated blood serum LH concentration. Secondly, a subcutaneous dose of an extended release composition effective for treating CPP for about six months is administered if the pediatric patient has a peak stimulated blood serum LH concentration of >5 IU/L. The extended release composition comprises N-methyl-2-pyrrolidone (NMP), Leuprolide or a pharmaceutically acceptable salt thereof; and a biodegradable polymer comprising polymer segments selected from 85:15 poly(lactide-co-glycolide) (PLG) copolymer segments, 85:15 poly(lactic acid-co-glycolic acid) (PLGA) copolymer segments, or a combination thereof, wherein the polymer has substantially no titratable carboxylic acid groups and wherein at least one distal end group of the polymer is hydroxyl-terminated. Thirdly, an additional injection of the stimulation composition is administered to the pediatric patient at about three to about six months after administering the extended release composition to confirm suppression of blood serum LH concentration to pre-pubertal level of <4 IU/L, wherein a blood sample from the pediatric patient is obtained within about at least thirty minutes of administering the subsequent stimulation composition for measuring a peak stimulated blood serum LH concentration. Lastly, the second and third steps may be repeated as necessary to treat CPP if the peak stimulated blood serum LH concentration of the third step at about three to about six months after the second step is <4 IU/L. The dose of the extended release composition is not individualized for the pediatric patient and upon contact of the extended release composition with a bodily fluid, the solvent dissipates and an in situ solid depot forms. The extended release formulation reduces the peak stimulated blood serum LH concentration of the pediatric patient to a pre-pubertal concentration level of <4 IU/L.

In another embodiment of the invention, a kit comprising at least one dose of an injectable stimulation composition and at least one dose of an injectable extended release composition is provided for the treatment of a child of at least two years of age who has CPP along with instructions for use thereof. The stimulation composition dose comprises GnRH or a GnRH agonist, or a pharmaceutically acceptable salt thereof, effective for measuring the peak stimulated blood serum LH concentration within the child. The extended release composition dose comprises the organic solvent N-methyl-2-pyrrolidone (NMP), about 40 mg to about 50 mg of leuprolide acetate or a pharmaceutically acceptable salt of leuprolide, and a biodegradable polymer. The biodegradable polymer comprises polymer segments selected from 85:15 poly(lactide-co-glycolide) (PLG) copolymer segment, 85:15 poly(lactic acid-co-glycolic acid) (PLGA) copolymer segment, poly(lactide) (PL) polymer segments, poly(lactic acid) (PLA) polymer segments, or a combination thereof. The biodegradable polymer has substantially no titratable carboxylic acid groups and at least one distal end group of the polymer is hydroxyl-terminated. The extended release composition dose is effective for the treatment of CPP in the child by reducing the peak stimulated blood serum LH concentration to a pre-pubertal concentration level of <4 IU/L when administered about once every six months. Upon contact with a bodily fluid, NMP in the extended release composition dissipates, such that an in situ solid depot forms. The kit further comprises instructions for the use thereof for treating CPP in a child.

In another embodiment of the invention, a kit comprising at least one dose of an injectable stimulation composition and at least one dose of an injectable extended release composition is provided for the treatment of a pediatric patient two years of age or older who has CPP along with instructions for use thereof. The stimulation composition dose comprises GnRH or a GnRH agonist, or a pharmaceutically acceptable salt thereof, effective for measuring the peak stimulated blood serum LH concentration within the pediatric patient. The extended release composition dose comprises the organic solvent N-methyl-2-pyrrolidone (NMP), about 40 mg to about 50 mg of leuprolide acetate or a pharmaceutically acceptable salt of leuprolide, and a biodegradable polymer. The biodegradable polymer comprises polymer segments selected from 85:15 poly(lactide-co-glycolide) (PLG) copolymer segment, 85:15 poly(lactic acid-co-glycolic acid) (PLGA) copolymer segment, or a combination thereof. The biodegradable polymer has substantially no titratable carboxylic acid groups and at least one distal end group of the polymer is hydroxyl-terminated. The extended release composition dose is effective for the treatment of CPP in the pediatric patient by reducing the peak stimulated blood serum LH concentration to a pre-pubertal concentration level of <4 IU/L when administered about once every six months. Upon contact with a bodily fluid, NMP in the extended release composition dissipates, such that an in situ solid depot forms. The kit further comprises instructions for the use thereof for treating CPP in a pediatric patient.

In some embodiments, a kit comprising a stimulation composition further comprising at least one GnRH agonist or pharmaceutically salt thereof selected from a group consisting of leuprolide, gonadorelin, goserelin, histrelin, nafarelin, buserelin, and triptorelin. In some embodiments, a kit comprising a pre-filled syringe(s), a pre-filled vial(s), or a combination thereof further containing an amount of a GnRH solution sufficient for administering a subcutaneous dose of either: 1) about 2.5 μg per kg of the child's body weight or 2) about 100 μg total. In some embodiments, a kit comprising a pre-filled syringe(s), a pre-filled vial(s), or a combination thereof further containing an amount of a leuprolide acetate solution sufficient for administering a subcutaneous dose of either: 1) about 10 μg to about 20 μg per kg of the child's body weight or 2) about 500 μg to about 1000 μg total. In some embodiments, a kit comprising a pre-filled syringe(s), a pre-filled vial(s), or a combination thereof further containing an amount of a nafarelin acetate solution sufficient for administering a subcutaneous dose of either: 1) about 1 μg per kg of the child's body weight or 2) about 100 μg total. In some embodiments, a kit comprising a pre-filled syringe(s), a pre-filled vial(s), or a combination thereof may contain an amount of a buserelin solution sufficient for administering a subcutaneous dose of about 100 μg total. In some embodiments, a kit comprising a pre-filled syringe(s), a pre-filled vial(s), or a combination thereof may contain an amount of a triptorelin acetate solution sufficient for administering a subcutaneous dose of about 100 μg total.

In some embodiments, the kit may include one or more doses of both the stimulation composition and the extended release composition sufficient to treat a child of at least 2 years of age with CPP for a time period of about 6 months, of about 12 months, of about 18 months, of about 24 months, or longer. In other embodiments, the kit may include one, two, three, four, five, six, seven, eight, nine, or more doses of the stimulation composition. In other embodiments, the kit may include one, two, three, four, or more doses of the extended release composition. In some embodiments, the extended release composition comprises an injection dose volume of about 0.375 mL. In some embodiments, each dose of the stimulation composition may be packaged individually or together into one or more pre-filled sterile vials, one or more pre-filled syringes, or a combination thereof. In other embodiments, each dose of the extended release composition may be packaged individually into a pre-filled single syringe, a pre-filled two-syringe system, or a combination thereof.

In some embodiments, the kit may comprise a two-syringe system consisting of a first syringe containing about 45 mg of lyophilized leuprolide acetate or an equivalent amount of a different pharmaceutically acceptable salt of leuprolide and a second syringe containing a solution of about 165 mg of about 85:15 poly(lactide-co-glycolide) (PLG) copolymer segments dissolved in about 165 mg of N-methyl-2-pyrrolidone (NMP). In the two-syringe system, the first syringe can be connected to the second syringe such that a passageway is formed between the first syringe and the second syringe to allow the passage of a flowable composition from one syringe to the other syringe. In some embodiments of the two-syringe system, the extended release composition is prepared by continuously mixing the contents of the second syringe back and forth into the contents of the first syringe of the interconnected two-syringe system for at least about 45 seconds or about 60 seconds to form a uniform suspension.

In some embodiments, the kit may comprise needles, alcohol swabs, and blood sample collection vials, together with additional instructions and labels for the use thereof.

DETAILED DESCRIPTION OF THE INVENTION

Figure 1:
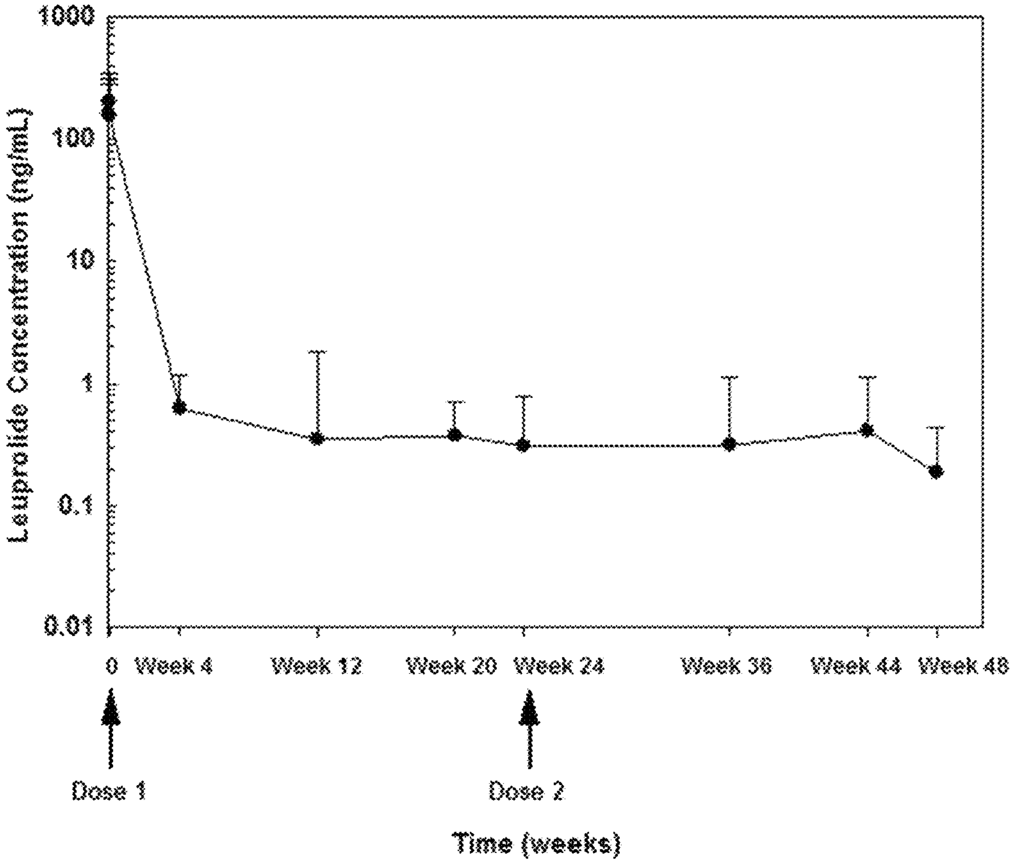
FIG. 1 is a chart showing the blood serum leuprolide concentrations from children with CPP undergoing a 12-month treatment period consisting of two doses (Week 0 and Week 24) of an extended release composition of the invention comprising 45 mg of leuprolide acetate.
Figure 2:
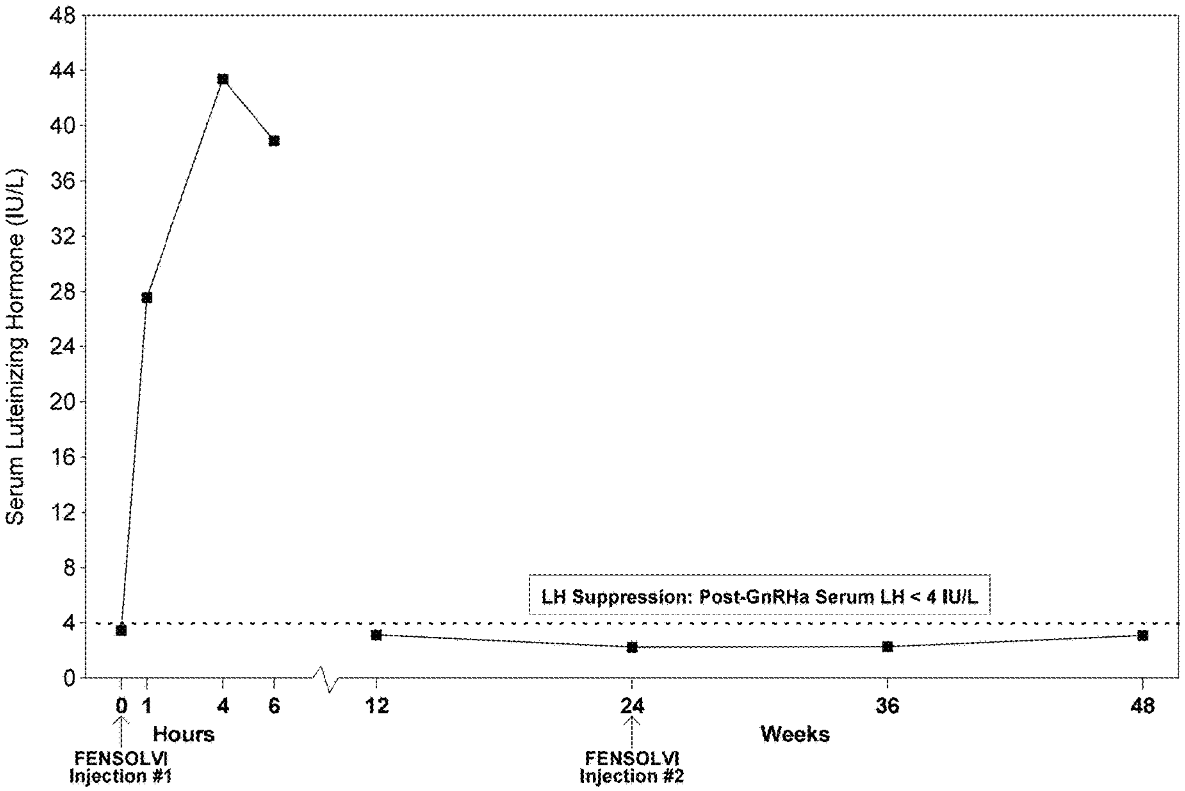
FIG. 2 is a chart plotting the blood serum LH concentration over time of children with CPP undergoing a 12-month treatment period consisting of two doses (Week 0 and Week 24) of an extended release composition of the invention comprising 45 mg of leuprolide acetate. The plot shows a transient surge in LH concentration associated with the initial 'burst' phase release of leuprolide acetate immediately following start of treatment (left side) and the sustained reduction of LH concentration associated with the continuous extended release of leuprolide acetate during the course of treatment (right side).
Figure 3:
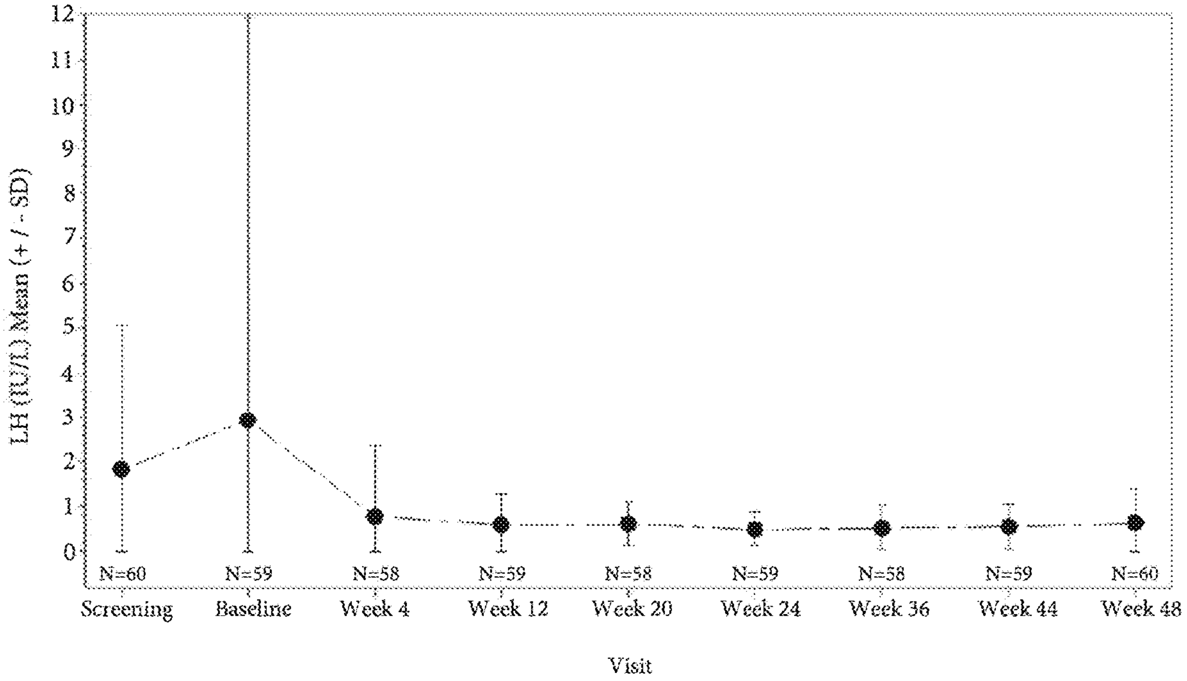
FIG. 3 is a chart plotting the mean peak stimulated blood serum LH concentration over time, of children with CPP undergoing a 12-month treatment period consisting of two doses (Week 0 and Week 24) of an extended release composition of the invention comprising 45 mg of leuprolide acetate.
Figure 4:
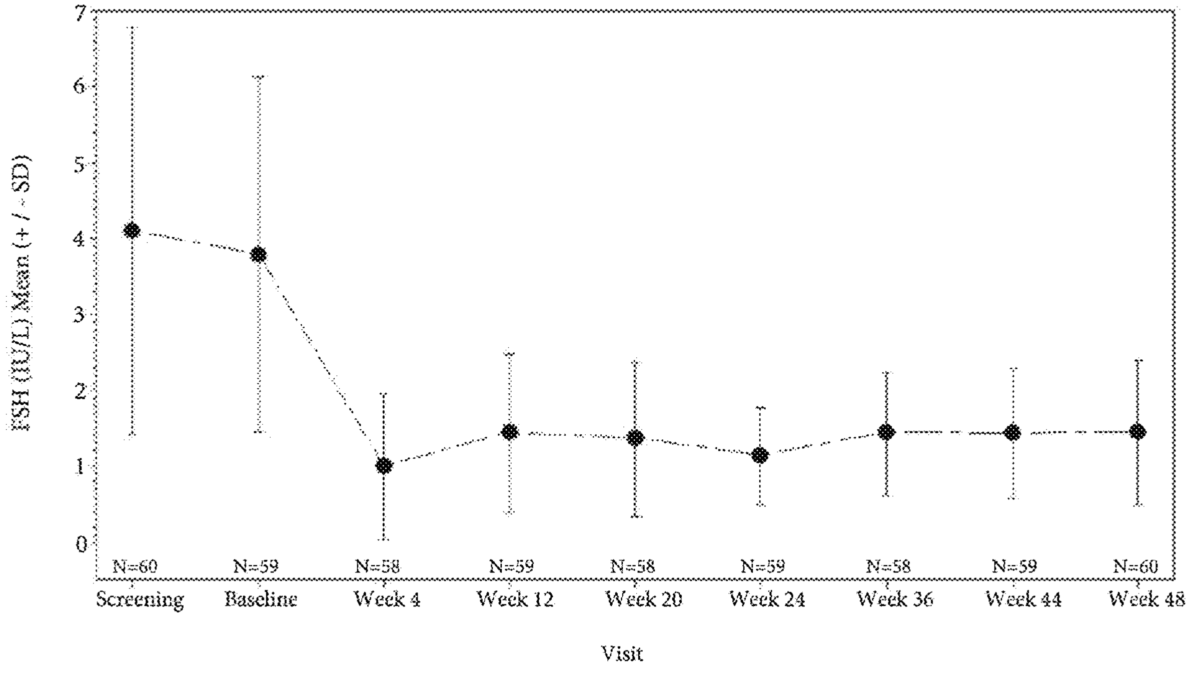
FIG. 4 is a chart plotting the mean peak stimulated blood serum FSH concentration over time, of children with CPP undergoing a 12-month treatment period consisting of two doses (Week 0 and Week 24) of an extended release composition of the invention comprising 45 mg of leuprolide acetate.
Figure 5:
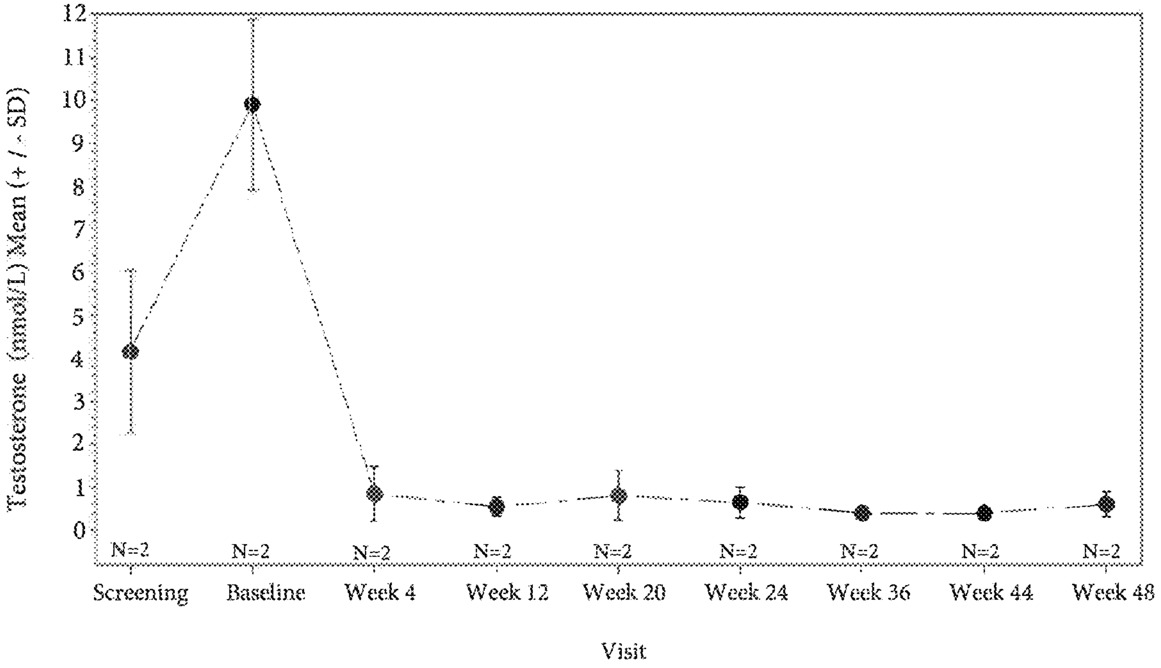
FIG. 5 is a chart plotting the mean peak stimulated blood serum testosterone concentration over time, of male children with CPP undergoing a 12-month treatment period consisting of two doses (Week 0 and Week 24) of an extended release composition of the invention comprising 45 mg of leuprolide acetate.
Figure 6:
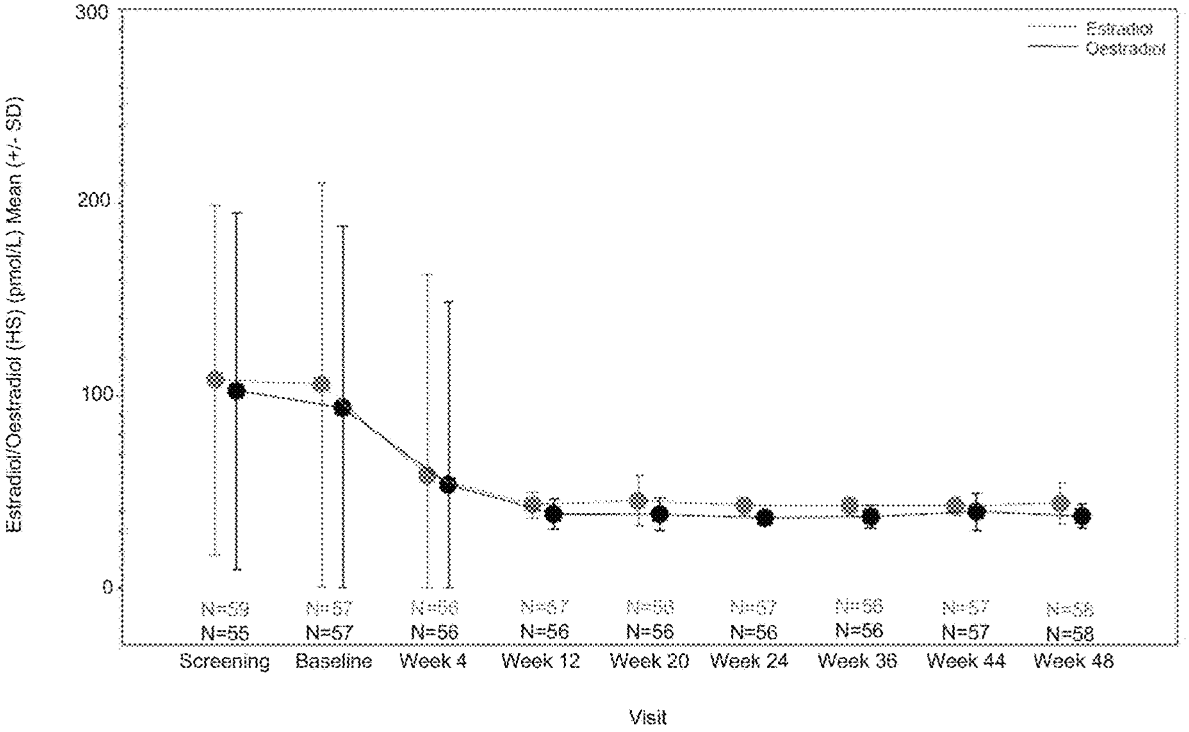
FIG. 6 is a chart plotting the mean peak stimulated blood serum estradiol, also known as oestradiol, concentration over time, of female children with CPP undergoing a 12-month treatment period consisting of two doses (Week 0 and Week 24) of an extended release composition of the invention comprising 45 mg of leuprolide acetate. Estradiol/oestradiol measured from same samples by either immunoassay (grey curve) or LC-MS/MS (black curve).
Figure 7:
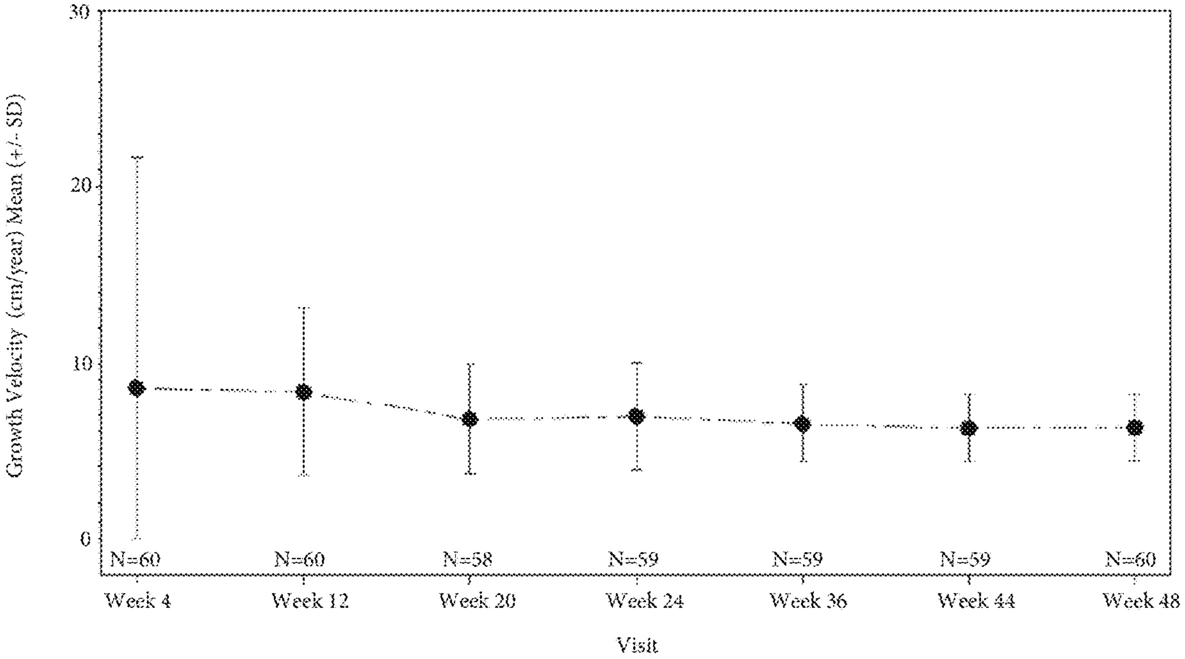
FIG. 7 is a chart plotting the mean growth velocity over time, of children with CPP undergoing a 12-month treatment period consisting of two doses (Week 0 and Week 24) of an extended release composition of the invention comprising 45 mg of leuprolide acetate.

Reference will now be made in detail to certain embodiments and features of the invention, examples of which are illustrated in the accompanying structures and formulas. While embodiments of the invention will be described in conjunction with the enumerated claims, it will be understood that it is not intended to limit the claimed invention to those examples. On the contrary, the invention is intended to cover all alternatives, modifications, and equivalents which may be included within the scope of the present invention as defined by the claims.

The present invention provides for methods and a kit useful for the effective treatment of pediatric patients 2 years of age and older with central precocious puberty (CPP) (i.e, in a child of at least 2 years of age with CPP) by means of administering a subcutaneous injection of an extended release composition comprising a biodegradable polymer capable of providing for the extended release of a GnRH or a GnRH agonist medicament in vivo for about 6 months. The present invention details use of this flowable composition to provide an in situ biodegradable depot within a child with CPP for effective treatment thereof via modulating the Hypothalamic-Pituitary-Gonadal axis (HPG) axis to establish hypogonadism within the child. Furthermore, the present invention and kit includes the optional use of a stimulation composition comprising a GnRH agonist for use in properly diagnosing whether a child has CPP and for measuring the effectiveness of the extended release composition in establishing and maintain hypogonadism within said child for the treatment of CPP over the course of the effective treatment period. The methods and kit of the present invention represent an advantageous improvement over existing approaches as a simpler to prepare, long acting, easier to administer, fixed dose therapeutic treatment for CPP offering enhanced efficacy and better patient care and comfort.

As described in more detail below, the inventors of the present application have discovered that an extended release composition comprising a biodegradable polymer with fixed dose of leuprolide acetate, a GnRH agonist, is effective for the treatment of CPP in a child of at least 2 years of age in need thereof, when administered once per about six months. The extended release formulation is administered subcutaneously in a small volume of 0.375 mL as a flowable, liquid formulation, which forms a solid, biodegradable in situ depot upon contact with bodily fluids. The extended release formulation is an effective treatment of CPP in a child by establishing hypogonadism for a period of at least 6 months through the continuous long-term extended release of leuprolide acetate into the body as the biodegradable polymer degrades. The smaller injection dose volume and subcutaneous route of administration are advantageous factors over current approaches. For example, LUPRON DEPOT-PED® 1-month and 3-month formulations requires deep intramuscular injection dose volumes of 1.0 and 1.5 mL, respectively. TRIPTODUR®, effective for 6 months, requires deep intramuscular injection dose volumes of 2.0 mL. SUPPRELIN LA® is a 3 mm by 3.5 cm subcutaneous surgical implant requiring extensive physician training and preparation for proper incision, implantation, and suturing close the entry wound opening. After implantation, SUPPRELIN LA® remains palpable underneath the skin and is associated with considerable physical and psychological pain. Therefore, the smaller injection dose volume, subcutaneous route of administration, and lack of surgical implantation associated with the extended release composition of the present invention disclosed herein offers significant benefits in offering easier physician preparation and administration (i.e. faster subcutaneous injection vs slower deep intramuscular injection; non-surgical vs surgical), as well as lowering the physical and psychological pain associated with treatment. Subcutaneous injection is preferred over intramuscular injection due to reduced likelihood of bone or nerve injury and intramuscular hematomas. Therefore, the extended release composition of the invention affords better patient care and compliance with therapeutic care and management by improving tolerability in pediatric patients. Lastly, unlike other leuprolide formulations, such as LUPRON DEPOT-PED® 1-month or 3-month, the extended release composition of the invention disclosed herein does not require the dosage to be continuously individualized for each child depending upon their weight or the clinical response of the child to therapy.

The term "extended release composition" may be used interchangeably with, but not limited to, "controlled release composition", "prolonged release composition", "therapeutic dose", "effective dose", "dose for the treatment of CPP", "treatment regimen", or any further variations thereof. The extended release composition is defined as a subcutaneously injectable liquid polymeric formulation comprising an organic solvent, a biodegradable polymer, and leuprolide or a pharmaceutically acceptable equivalent or salt thereof, which forms an in situ solid depot useful for the treatment of CPP in a child via the continuous release of leuprolide into the body over a 6-month period.

Similarly, the term "stimulation composition" may be used interchangeably with, but not limited to, "stimulation test", "diagnostic dose", "screening dose", "dose for the diagnosis of CPP", "test for CPP", or any further variations thereof. The stimulation composition is defined as a subcutaneously injectable solution of GnRH or a GnRH agonist useful in stimulating the release of CPP-associated hormones.

As used herein, the term "Hypothalamic-Pituitary-Gonadal axis (HPG)" refers to the collective entity formed by these three separate endocrine glands. HPG plays a critical role in human development through the controlled regulated release of GnRH, gonadotropins, and sex hormones. Abnormal HPG activity can lead to associated disease states. For instance, premature release of GnRH or gonadotropins can initiate early pubertal development in children (i.e. precocious puberty), which can be identified by secondary sexual and physical characteristics. The term "secondary sexual characteristics" refers to the development and appearance of physical anatomical and physiological sexual features within a male or a female during puberty. Puberty is the process of sexual maturation within an individual, as they enter transition from childhood through adolescence into adulthood. In females, puberty, generally, occurs between ages 8 to 13. In males, puberty generally occurs between ages 9.5 to 13.5. Puberty or pubertal development is initiated upon signaling of gonadotropins from the pituitary, which in turn stimulates the production and release of additional sex hormones from the gonads. Secondary sexual characteristics may include, but are not limited to, changes in a child's brain, bones, muscle, blood, skin, hair, breasts, height, weight, head size, growth rate, metabolic activity, sex organs, or other pubertal associated anatomical and physiological changes. The term secondary sexual characteristics may be used synonymously herein with terms such as "sexual characteristics", "sexual maturation", "pubertal development", or any other analogous meaning. However, none of those terms should be confused with the term "primary sexual characteristic", which is defined herein as the gonadal composition of an individual from birth as generally determined by the individual's chromosomal composition (i.e. XX or XY sex chromosomes).

As used throughout the present invention, the term "child" may be used interchangeably with, "child of at least 2 years of age" or a "pediatric patient 2 years of age and older", and is defined as any child ages 2 to 12 years old. A child with early onset of pubertal signs and symptoms associated with CPP may be also referred to as a "child with CPP", a "pediatric patient with CPP" or "pre-pubertal child". These children are defined as male children typically ages 2 to 9 years old or female children typically ages 2 to 8 years old, which display pubertal signs or symptoms associated with CPP, such as abnormal gonadotropin and/or sex hormone levels, and/or secondary sexual characteristics. Effective treatment of CPP in a child includes establishing "hypogonadism" which is defined as a decrease in the functional activity of the gonads (i.e. testes or ovaries), which may further result in decreased production or release of sex hormones. In some instances, low androgen (i.e. testosterone) levels may be termed as "hypoandrogenism" while low estrogen (i.e. estradiol) levels may be termed as "hypoestrogenism". The term "hypogonadism," may also be used to refer to a return to a normal pre-pubertal state (e.g. suppressed LH and FSH, and subsequently estradiol and testosterone) for a child with CPP under effective treatment.

Importantly, determining whether a child has CPP versus PPP is useful in establishing proper and effective treatment of care for said child in need thereof. Differential diagnosis of CPP vs PPP can be achieved through use of a stimulation test comprising a subcutaneous injection of GnRH or a GnRH agonist to a child suspected of having PP (Carretto, F., et al. "The usefulness of the leuprolide stimulation test as a diagnostic method of idiopathic central precocious puberty in girls." Horm. Metab. Res. 2014; 46(13):959-963). Administration of a GnRH agonist, for instance an aqueous solution of leuprolide acetate, results in a transient change in the peak stimulated blood serum concentrations of various sex hormones. Blood samples may be obtained from the child within about 3 hours, but can be readily obtained between thirty minutes to about 1 hour following administration of the GnRH agonist stimulation test. Obtained blood samples can be used to measure the concentration of various CPP-associated sex hormones including, but not limited to, LH, FSH, testosterone, and estradiol. Peak stimulated blood serum concentrations of LH of >5 IU/L at about thirty minutes or later post GnRH agonist stimulation may be considered to be diagnostic for CPP.

Additional supportive diagnostic criteria for CPP include a combination of clinical and physical parameters recorded before initiating treatment including, but not limited to, Tanner stage and bone age. As used herein, the term "Tanner stage" may be used interchangeably with "Tanner scale". Tanner stage is a scaling of a child's physical development by measuring primary and secondary sex characteristics. Tanner stages are not representative of chronological age but, rather, is/are used to evaluate pubertal maturity. Conversely, the term "bone age" may be used synonymously with "bone age ratio" or "ratio of bone age to chronological age" and is defined as the child's anatomical bone age (as determined by methods such as X-ray analysis of the non-dominant hand, from which bone length and epiphyseal plate size are used by the Greulich and Pyle method to determine bone age) when compared to the child's chronological age (Antoniazzi, F., et. al. "Central precocious puberty: current treatment options." Paediatr. Drugs. 2004; 6(4):211-231). A bone age ≥1 years of chronologic age is indicative of accelerated bone growth (Carel, J. C., et. al. "Clinical practice. Precocious puberty." N Engl J Med. 2008; 358(22):2366-2377). Idiopathic CPP can be further distinguished from organic CPP by way of secondary laboratory testing such as neurological examination and physical examination. MRI scans can be employed to verify absence of any tumors. Physical examinations may be used to check for other signs and symptoms; for instance, the presence of light brown patches of skin called café-au-lait spots associated with McCune-Albright syndrome, which is connected to PPP.

Various long-lasting release polymer formulations with desirable flowable properties for extended release of therapeutic compounds have been described previously. Polymer formulations with flowable properties have advantageous properties, including but not limited to, ease of administration, stability, and release kinetics. One such extended release polymer composition used in the present invention comprises a biodegradable, water-insoluble polymer or copolymer and a therapeutic compound, such as a GnRH agonist (i.e. leuprolide acetate), dispersed in a biocompatible organic solvent. Upon administration as a flowable, liquid state suspension via subcutaneous injection, the extended release composition solidifies as a semi-solid to solid mass in situ depot. As used herein, the term "in situ depot" may be used interchangeably with "implant", or "solid mass". The in situ depot may be defined as the resulting product of the extended release composition of the present invention, which upon administration into a bodily or aqueous fluid begins to solidify into a solid mass via coagulation and/or precipitation of the polymer-GnRH agonist mixture as the biocompatible organic solvent dissipates or diffuses away from the polymer-GnRH agonist mixture, and into the host tissues. This remaining solid mass serves as an extended release depot allowing for a continuous, steady-state diffused release of the therapeutic compound into the body as the biodegradable polymer degrades over a period of about 6 months (or about 24 weeks).

Leuprolide or any pharmaceutically acceptable equivalent or salt thereof, is a synthetic GnRH agonist peptide analog, shown to be effective for use in treating CPP by reducing blood serum concentrations of CPP-associated hormones, such as LH and FSH (Kim, Y. J., et al. "Multicenter clinical trial of leuprolide acetate depot (Luphere depot 3.75 mg) for efficacy and safety in girls with central precocious puberty." Ann Pediatr Endocrinol Metab. 2013; 18(4):173-178). Suppression of LH and FSH from the anterior pituitary is reversible in nature upon discontinuation of therapy. Leuprolide acts upon pituitary GnRH receptors. Leuprolide equivalents, such as leuprolide acetate, have been demonstrated to increase and/or restore projected adult height, as well as protecting from psychosocial harm associated with early onset of pubertal symptoms. Leuprolide acetate has been shown to be safe and effective for use in prostate cancer with doses as high as 20 mg/day for up to 2 years caused no adverse effects differing from those observed with a 1 mg/day dose over 2 years.

In one embodiment of the invention, the extended release composition is used for the treatment of CPP in a child of at least 2 years of age and comprises a biocompatible organic solvent, the GnRH agonist leuprolide or a pharmaceutically acceptable salt thereof, and a biodegradable polymer, which forms an in situ solid depot upon administration into the body and subsequently provides for effective treatment against CPP in a child for about 6 months (or about 12 weeks). Components of the extended release composition are described in greater detail below.

Solvent:

As used herein, the term "biocompatible organic solvent" may be defined as any carbon based solvent safe for injection within a human body, preferably safe within a child of at least 2 years of age. The term "biocompatible organic solvent" may be used interchangeably with terms such as, but not limited to, "organic solvent", "solvent", or "base fluid". The biocompatible solvent may be homogenous or heterogeneous in nature. The organic solvent may be a polar aprotic solvent, which is generally non-toxic in bodily fluids. The organic solvent may be partially to completely water-insoluble.

In some embodiments of the invention, the biocompatible organic solvent may be any organic solvent, which may be capable of dissolving the biodegradable polymer and then forming a suspension with the GnRH or a GnRH agonist, such as leuprolide acetate, when the three components are combined. Furthermore, the biocompatible organic solvent may be any organic solvent, which may partially or completely dissipate or diffuse into host surrounding tissues upon administration thereof. Diffusion or dissipation of the organic solvent upon administration into bodily fluids allows for solidification of the polymer and GnRH or GnRH agonist as a solid (i.e. non-liquid) mass via coagulation or precipitation of both components within bodily fluids. The extent of water insolubility of the organic solvent may be adjusted depending upon the desired rate of diffusion into bodily fluids for controlling the rate and scope of polymer solidification. Furthermore, the degree of water-insolubility of the organic solvent may be adjusted in order to control the viscosity of the flowable extended release composition, which is important for ease of preparing and administering the extended release composition.

In some embodiments, the biocompatible organic solvent may be at least partially made up of one or more organic solvents selected from the group consisting of amides, acids, alcohols, esters of monobasic acids, ether alcohols, sulfoxides, lactones, polyhydroxy alcohols, esters of polyhydroxy alcohols, ketones, and ethers.

In some embodiments, the biocompatible organic solvent may be at least partially made up of one or more organic solvents selected from the group consisting of N-methyl-2-pyrrolidone (NMP), 2-pyrrolidone, N-ethyl-2-pyrrolidone, N-cyclohexyl-2-pyrrolidone, N-hydroxyethyl-2-pyrrolidone, dimethyl acetamide, dimethyl formamide, acetic acid, lactic acid, ethanol, propanol, methyl lactate, ethyl lactate, methyl acetate, diethylene glycol monomethyl ether, glycofurol, glycerol formal, isopropylidene glycerol, dimethyl sulfoxide, e-caprolactone, butyrolactone, propylene glycol, polyethylene glycol, glycerol, 1,3-butyleneglycol, methoxypolyethylene glycol, methoxypropylene glycol, acetone, methyl ethyl ketone, and tetrahydrofuran.

In some embodiments, the organic solvent selected for use in the extended release composition for treating CPP is N-methyl-2-pyrrolidone (NMP). In some embodiments of the invention, about 100 mg, about 105 mg, about 110 mg, about 115 mg, about 120 mg, about 125 mg, about 130 mg, about 135 mg, about 140 mg, about 145 mg, about 150 mg, about 155 mg, about 160 mg, about 165 mg, about 170 mg, about 175 mg, about 180 mg, about 185 mg, about 190 mg, about 195, or about 200 mg of NMP may be used in the extended release composition. In some instances, about 165 mg of NMP may be used as the organic solvent for the extended release composition. In some embodiments of the invention, the amount of NMP used in the extended release composition may represent about 40%, about 41%, about 42%, about 43%, about 44%, about 45%, about 46%, about 47%, about 48%, about 49%, or about 50% of the extended release composition based upon weight to weight (w:w). In some instances, the extended release composition comprises about 44% w:w of NMP.

GnRH or GnRH Agonist:

As used herein, the term "GnRH" may refer to "gonadotropin releasing hormone". GnRH is a natural, endogenous neuro-hormone released from the hypothalamic region of the human brain. GnRH acts upon GnRH receptors located in the pituitary region of the human brain, stimulating the synthesis and systemic release of gonadotropins from the pituitary. GnRH is a peptide hormone that targets other non-originating endocrine glands. GnRH is synthesized by the human gene GNRH1 as a preprohormone, which is subsequently processed to final form under regulation by the Hypothalamic-Pituitary-Gonadal axis. The sequence of "GnRH" is readily known and available. GnRH is secreted from the hypothalamus in a pulsatile manner. "GnRH" concentration, and thus functional activity, is very low during normal childhood. Pubertal entry into adolescence is associated with an increase in GnRH levels and related activity.

The term "GnRH agonist", as used herein, may be defined as any substance which mimics the structure and/or functional activity of GnRH, such as by binding to and activating a GnRH receptor. GnRH agonists may be peptides or small molecule drugs. GnRH may be used interchangeably with, but not limited to, the terms "GnRHa", "GnRH analog", "GnRH ligand", "GnRH synthetic mimetic", or "GnRH modulator". The term GnRH agonist may be further used synonymously with the broader term GnRH. GnRH agonists may be natural and/or synthetic in nature. GnRH agonists may be endogenous or exogenous in nature. GnRH agonists act upon GnRH receptors in an excitatory fashion to stimulate release of gonadotropins from gonadotrope cells located within the pituitary region of the brain. However, prolonged exposure to GnRH or GnRH agonists leads to GnRH receptor desensitization and down regulation, leading to "hypogonadism".

In some embodiments of the invention, the GnRH or GnRH agonist(s) used within the extended release composition may be a peptide or small molecule drug capable of mimicking the functional activity of GnRH to bind and modulate GnRH receptors. The GnRH or GnRH agonist(s) may be either natural or synthetically made, as well as endogenous or exogenous in source. Examples of GnRH agonists may include, but are not limited to, leuprolide (leuprorelin), gonadorelin, goserelin, histrelin, nafarelin, buserelin, triptorelin, or any known pharmaceutically acceptable equivalents or salts thereof. The sequences of GnRH or any GnRH agonist are readily known and available.

In one embodiment of the invention, the extended release composition comprises leuprolide or a pharmaceutically acceptable equivalent or salt thereof as the active pharmaceutical ingredient (API). Leuprolide is a synthetic GnRH agonist peptide analog effective for use in treating CPP by reducing blood serum concentrations of CPP-associated gonadotropins and/or sex hormones. Leuprolide acts similarly to GnRH upon GnRH receptors. Prolonged exposure to leuprolide can establish hypogonadism within an individual with suppression of gonadotropins LH and FSH from the anterior pituitary, being reversible in nature upon discontinuation of leuprolide exposure.

Known pharmaceutically equivalents (i.e. derivatives of leuprolide) include, but are not limited to leuprolide 6NMeDLeu, leuprolide 8NMeArg, leuprolide 3NMe1Nal, leuprolide 2 Phe, leuprolide 2NMeHis, leuprolide 2NMePhe, leuprolide 10SarNH2, leuprolide-ethyl-D5, leuprolide 5NMeTyr, leuprolide 7NMeLeu, leuprolide 4NMeSer, and leuprolide 3-1Nal. The sequences and chemical structures of any of these leuprolide derivatives are readily known and available. In some embodiments of the invention, unmodified leuprolide is the form used in the extended release composition.

Known pharmaceutically acceptable salts of leuprolide include, but are not limited to, leuprolide acetate, leuprolide monoacetate, leuprolide oleate, leuprolide palmitate leuprolide mesylate, leuprolide trifluoracetic acid (TFA), leuprolide trifluoroacetate, leuprolide (5-9), (D-His2)-leuprolide trifluoracetic acid (TFA), leuprolide hydrochloric acid (HCL), leuprolide-D5 acetate, and leuprolide (L-Leu). The sequences and chemical structures of any of these leuprolide salts are readily known and available. In some embodiments of the invention, leuprolide acetate is the salt form used in the extended release composition.

In some embodiments of the invention, about 40 mg, about 41 mg, about 42 mg, about 43 mg, about 44 mg, about 45 mg, about 46 mg, about 47 mg, about 48 mg, about 49 mg, or about 50 mg of a leuprolide acetate may be used in the extended release composition. In some instances, about 45 mg of leuprolide acetate may be used in the extended release composition. In some embodiments of the invention, the amount of leuprolide acetate used in the extended release composition may represent about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, or about 20% of the extended release composition based upon w:w. In some instances, the extended release composition comprises about 12% w:w of leuprolide acetate.

As used herein, the term "free base equivalent" may refer to the conjugate base or deprotonated form of an amine containing compound or substance. For instance, 42 mg of leuprolide represents the free base equivalent of 45 mg of leuprolide acetate. In some embodiments, the amount of leuprolide or the pharmaceutically acceptable equivalent or salt thereof in the extended release composition may be about 40 mg, about 41 mg, about 42 mg, about 43 mg, about 44 mg, about 45 mg, about 46 mg, about 47 mg, about 48 mg, about 49 mg, or about 50 mg leuprolide free base equivalent. In some instances, the amount of leuprolide or the pharmaceutically acceptable equivalent thereof in the extended release composition may be about 42 mg leuprolide free base equivalent.

As used herein, the term "GnRH receptor" may be defined as a gonadotropin releasing hormone receptor present upon the surface of gonadotrope cells located in the pituitary region of the human brain. GnRHR can also be found in additional tissues such as lymphocytes, breast, ovarian, and prostate. In some cases, GnRH receptor may be used interchangeably with "GnRHR" or "luteinizing hormone releasing hormone receptor (LHRHR)". However, it is important to note that the term LHRHR should not be confused with the term LHR, which, as defined in greater detail below, is responsible for binding LH. GnRH receptors are synthesized, in two major forms, from the GNRHR and GNRHR2 genes. GnRH receptors are coupled to G-proteins, which propagate signal transduction into the host cell upon binding of GnRH or a GnRH agonist to the GnRH receptor. Activation of GnRH receptors (i.e. LHRHR) by GnRH binding leads to synthesis and release of gonadotropins and sex hormones from the gonadotrope cells from the pituitary region of the brain into the body systemically. In response to GnRH or GnRH agonist binding, GnRH receptors may be regulated through such generalized mechanisms including, but not limited to, 1) Transient Upregulation, 2) Desensitization, 3) Downregulation, and/or 4) Modulation. The sequences of either GnRH receptor forms are readily known and available.

As used herein, the term "gonadotrope" or "gonadotrope cell(s)" may be used to refer to an endocrine cellular line capable of producing and releasing gonadotrophins. Gonadotrope may be used interchangeably with "gonadotrophic cell". Gonadotrope cells are located primarily in the anterior pituitary region of the human brain and are regulated by extracellular GnRH or GnRH agonist binding to gonadotrophic cell surface GnRH receptors. Gonadotrophic cells may also be regulated by binding of extracellular sex hormones such as testosterone and estradiol.

As used herein, the term "gonadotropin(s)" may be defined as a class of glycoprotein polypeptide hormone(s) secreted by gonadotrope cells located within the anterior pituitary region of the human brain. Gonadotropin may be used interchangeably with, but not limited to, "Gn", "pituitary gonadotrophins", and in some instances, "pituitary hormones". Gonadotropins may include, but are not limited to, luteinizing hormone (LH), follicle-stimulating hormone (FSH), and chorionic gonadotropin (CG). Systemic release of gonadotropins into the body allows them to act upon the gonads (testes and ovaries) for the extended production of sex hormones and gametes. Gonadotropin secretion occurs in a pulsatile manner. Diminished release of gonadotropins results in hypogonadism. The sequence of any gonadotropin of interest is readily known and available.

In some embodiments, the administration of the GnRH agonist leuprolide or a pharmaceutically acceptable equivalent thereof as the active pharmaceutical ingredient (API) within the extended release composition may be used to activate GnRH receptors analogously to de novo GnRH. Similar to GnRH, stimulation of GnRHR by leuprolide or a pharmaceutically acceptable equivalent or salt thereof causes tyrosine phosphatase activation, which ultimately leads to the extracellular release of gonadotropins, such as LH and FSH, and the subsequent release of additional sex hormones. However, prolonged GnRHR exposure to leuprolide or a pharmaceutically acceptable equivalent thereof may be used to achieve suppression of the release of gonadotropins into the body systemically. Continuous exposure to leuprolide leads to GnRHR desensitization and down regulation. Therefore, the GnRH agonist leuprolide or a pharmaceutically acceptable equivalent thereof as the API within the extended release composition may be effectively used medically to establish hypogonadism within a child of at least 2 years of age with CPP.

In some embodiments, initial administration of leuprolide or a pharmaceutically acceptable equivalent thereof may lead to a transient excitatory activation of GnRHR that causes gonadotrope cells to release a temporary increase in gonadotropins into the body. This transient surge may be synonymously referred to as the initial 'flare-up' response and is likewise seen upon administration of GnRH and other GnRH agonists.

One advantage of the extended release composition of the present invention is that the amount of GnRH or GnRH agonist such as leuprolide or the pharmaceutically acceptable equivalent thereof in the extended release composition is independent from the weight of the child receiving treatment and/or is independent from the clinical response of the child during treatment. In particular, the amount of GnRH or GnRH agonist such as leuprolide or the pharmaceutically acceptable equivalent thereof in the extended release composition is not modified from the initial to subsequent administrations of the extended release composition to the child. In other words, the extended release composition of the invention provides a fixed dose of the GnRH or GnRH agonist to all children treated with the composition that is not modified during the course of treatment, regardless of the weight of the child, the clinical response of the child to the therapy, or any other possible associated factor. The absence of needing to adjust the amount of GnRH agonist within the extended release composition or the amount of the extended release composition itself, represents an improvement over LUPRON DEPOT-PED® 1-month and 3-month formulations, which, in contrast to the formulation of the invention, require the dosage to be continuously adjusted based upon the child's weight and/or clinical response to therapy, in order to achieve effective therapeutic treatment in each individual child. Therefore, the present invention benefits from providing a single, standard dosing regimen for the treatment of any child with CPP and facilitates the treatment of children with the condition with improved compliance.

Polymer:

As used herein, the term "polymer" may be defined as a macromolecular organic compound that is largely, but not necessarily exclusively, formed of repeating units covalently bonded in a chain, which may be linear or branched. A "repeating unit" is a structural moiety of the macromolecule that can be found within the macromolecular structure more than once. Typically, a polymer is composed of a large number of only a few types of repeating units that are joined together by covalent chemical bonds to form a linear backbone, from which substituents may or may not depend in a branching manner. The repeating units can be identical to each other but are not necessarily so. Therefore, a structure of the type -A-A-A-A- wherein A is a repeating unit is a polymer is known as a homopolymer. Whereas, a structure of the type -A-B-A-B- or -A-A-A-B-A-A-A-B- wherein A and B are repeating units, is also a polymer, and is sometimes termed a copolymer. A structure of the type -A-A-A-C-A-A-A or A-B-A-C-A-B-A wherein A and B are repeating units but C is not a repeating unit (i.e., C is only found once within the macromolecular structure) is also a polymer under the definition herein. When C is flanked on both sides by repeating units, C is referred to as a "core" or a "core unit." A short polymer, formed of up to about 10 repeating units, is referred to as an "oligomer." There is theoretically no upper limit to the number of repeating units in a polymer, but practically speaking the upper limit for the number of repeating units in a single polymer molecule may be approximately one million. However, in the polymers of the present invention the number of repeating units is typically in the hundreds. In some embodiments, the term "polymer" may be used interchangeably with the term "biodegradable polymer".

The term "copolymer" may be used to refer to a variety of polymers comprising non-identical repeating units. A "copolymer" may be regular or random in the sequence as defined by the more than one type of repeating unit. Some types of copolymers are random copolymers, graft copolymers and block copolymers.

Similarly, the term "polymer segment" or a "copolymer segment" as used herein may refer to a portion or moiety of a larger molecule wherein that segment is a section of a polymer or a copolymer respectively that is bonded to other portions or moieties to make up the larger molecule. When the polymer segment or a copolymer segment is attached to the larger molecule at only one end of the segment, the end of attachment is the "proximal end" and the other, free end is the "distal end."

In some embodiments of the invention, the biodegradable polymer used within the extended release composition may be a polymer of the general formula:

HO—(P)—C(═O)O—Ra-O(O═)C—(P)—OH wherein Ra is a core unit and P are polymeric segments. The biodegradable polymer of the invention may, in some embodiments, comprise polymeric segments selected from poly(lactide-co-glycolide) (PLG), poly(lactic acid-co-glycolic acid) (PLGA), polylactide (PL), poly(lactic acid) (PLA), or a combination thereof. In some embodiments, the polymer is formed by ring-opening polymerization of lactide and glycolide monomers initiated from the core unit using a suitable catalyst. Ring-opened lactide and glycolide monomers are covalently attached to the core unit via covalent linkages such that the polymer comprises no titratable carboxylic ends. In contrast to many polymers known in the art, the biodegradable polymer of the invention does not comprise any titratable carboxylic acid groups but, instead, comprises at least one hydroxyl-terminated distal end of the PLG, PLGA, PL, and/or PLA polymer segments. In some embodiments, as shown in the formula above, both ends of the co-polymer are hydroxyl-terminated.

The term "catalyst", as used herein, may refer to any suitable substance capable of initiating or and/or increasing the rate of polymerization. In some embodiments, the catalyst may be any catalyst suitable for ring-opening polymerization. For example, a tin salt of an organic acid may be used as the polymerization catalyst. The tin salt may be either in the stannous (divalent) or stannic (tetravalent) form. In some instances, the catalyst stannous octanoate may be used. The catalyst may be present in the polymerization reaction mixture in any suitable amount, typically ranging from about 0.01 to 1.0 percent.

The term "core" or "core unit" may be used herein to refer to a portion or moiety of a polymer that is not itself a copolymer segment, but is incorporated within the polymer chain and has at least one polymer or copolymer segment bonded to it. A core may be rendered into a chemically reactive species capable of polymerization upon contact with a suitable catalyst of choice. A core may be formed from a molecule that is incorporated into the polymer chain that grows from it during the polymerization reaction. A core may have two or more polymer or copolymer segments bonded to it.

In some embodiments, the core unit of the polymer may be an alkanediol. In some instances, the alkanediol used herein may be a saturated, branched or straight chain or cyclic alkanediol of about 4 to about 8 carbon atoms. An alkanediol may be converted into an alkane diradical having two monovalent radical centers derived by the removal of two hydrogen atoms from different carbon atoms of the parent alkanediol via a catalyst, wherein each monovalent radical center bears a hydroxyl group. Thus, an alkanediol is a dihydroxyalkane. Ring-opening polymerization of lactide and glycolide monomers initiated from an alkane diradical leads to monomeric attachment to the core unit via covalent ester linkages such that the polymer comprises no titratable carboxylic ends.

In some embodiments, alkanediols useful in the invention may include, but are not limited to: 1,4-butylene ($—CH_2CH_2CH_2CH_2—$), 2,3-butylene ($CH_3CHCHCH_3$), 1,6-hexylene ($—CH_2CH_2CH_2CH_2CH_2CH_2—$), 1,4-cyclohexanedimethyl ($—CH_2$-cyclohexyl-$CH_2—$), and the like. Therefore, in some further instances, typical alkanediols of the invention may include, but are not limited to, 1,4-butanediol ($HOCH_2CH_2CH_2CH_2OH$), 2,3-butanediol ($CH_3CH(OH)CH(OH)CH_3$), 1,6-hexanediol ($HOCH_2CH_2CH_2CH_2CH_2CH_2OH$), cyclohexane-1,4-dimethanol, and the like. In other instances, an alkanediol may be optionally substituted with other functional groups on the carbon atoms that form the alkane moiety, including but not limited to groups such as alkoxy, hydroxy, halo, cyano, carboxy, alkylcarboxy, carboxamido, alkyl or dialkyl carboxamido, alkyl or aryl thio, amino, alkyl or dialkyl amino, aryl, or heteroaryl. In some further embodiments, an α,ω-diol which refers to an alkanediol, wherein the two hydroxyl groups are disposed respectively on the two terminal carbon atoms of an alkane chain may be used as the core unit of the polymer (i.e. an α,ω-diol comprises two primary hydroxyl groups). Typical α,ω-diols may include, but are not limited to: 1,4-butanediol and 1,6-hexanediol. In some embodiments, the alkanediol of choice may be present within the polymerization reaction mixture in amounts ranging from about 0.05% to about 5.0%. In some instances, the amount of a selected alkanediol used within the polymerization reaction mixture is about 0.5% to about 2.0%. The greater the weight percentage, and thus the greater the mole fraction of the alkanediol in the polymerization reaction mixture, the shorter are the chain lengths of the polymers attached to the alkanediol core due to the decreased availability of lactide or glycolide reagent molecules per initiating hydroxyl group.

In other embodiments of the invention, the core unit of the polymer may be a mono-functional alcohol. Alcohols useful as core units in the invention include, but are not limited to, methanol, ethanol, or 1-dodecanol, which will provide a polymer with the core unit on one distal end as a terminal ester group and the other distal end as a hydroxyl group. In some embodiments of the invention, a biodegradable polymer formed using a monofunctional alcohol as the core unit may be a polymer of the general formula:

$$CH_3—(CH_2)_n—C(=O)O—(P)—OH$$

wherein n may be an integer and P is a polymeric segment.

As used herein, the term "lactide" may be used herein, when referring to the chemical compound itself, for example as the "lactide reagent" or "lactide reactant" means the dimer cyclic ester of lactic acid:

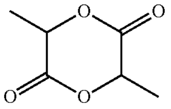

The lactide may be of any configuration at the chiral carbon atoms (bearing the methyl groups) within the meaning of the term herein. It may also be a mixture of molecules with different configurations at the chiral carbon atoms. Thus, lactide may be DD-, DL-, LD-, LL-lactide, or any mixture or combination thereof.

In some embodiments, when referring to a polymer such as a "poly(lactide-glycolide)' containing a "lactide" unit, the term "lactide" or "lactide unit" means the ring-opened species consisting of two lactic acid units joined by an ester bond which can be further incorporated into a polymeric chain with other such units or with other types of repeating units. One end of the lactide unit comprises a carboxyl group that may be bonded to an adjacent atom via an ester linkage, or an amide linkage, or via any other type of bond that a carboxyl group may form. The other end of the lactide unit comprises a hydroxyl group that may be bonded to an adjacent atom via an ester linkage, an ether linkage, or via any other type of bond that a hydroxyl group may form. A "lactide" in a poly-lactide polymer thus refers to the repeating unit of the polymer that can be viewed structurally as being formed from a pair of lactic acid molecules, with the understanding that the wavy lines indicate points of attachment to neighboring groups:

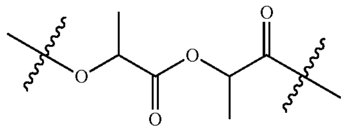

Again, the configuration at the chiral carbon atoms includes any and all possible configurations and mixtures thereof, as described above for the cyclic dimer.

The term "glycolide" may be used herein, when referring to the chemical compound itself, such as the "glycolide reagent" or the "glycolide reactant", to mean the dimer cyclic ester of glycolic acid:

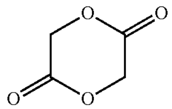

When referring to a "glycolide" unit in a polymer, the term refers to the repeating unit, a dimer of glycolic acid as shown:

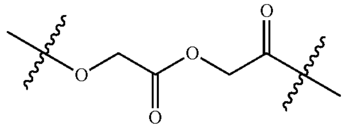

Similarly to the lactide unit, in some embodiments, one end of the glycolide unit may comprise a carboxyl group bonded to an adjacent atom via an ester linkage, or an amide linkage, or via any other type of bond that a carboxyl group may form, and the other end of the glycolide unit comprises a hydroxyl group that may be bonded to an adjacent atom via an ester linkage, an ether linkage, or via any other type of bond that a hydroxyl group may form.

It should be understood that those in the art comprehend that a "lactide" or a "glycolide" as used herein in either sense is itself a dimer of lactic acid or glycolic acid respectively, either cyclic or linear. In a polymer composed of such dimeric molecular species, the repeating unit as defined herein is therefore formally itself a dimer. Polymers of this type are referred to herein as "polylactide" or "poly(lactide-glycolide)". Furthermore, it is well-known that there are other polymers known in the art as "poly-lactic acid" or "poly-glycolic acid" that are formed from polymerization of the monomers, either lactate (lactic acid) or glycolate (glycolic acid). There are also copolymers known in the art as "poly(lactic acid-glycolic acid)" or "poly(lactate-glycolate)." In polymers of this type, the repeating unit is a monomer comprising lactic acid, glycolic acid, or both.

When a polymer is formed only of lactic units, or only of glycolic units, the distinction is relatively insignificant except as regards the method by which the polymer is made. However, when a polymer is formed of a mixture of lactic and glycolic units, the distinction is structurally important. For example, a polymer formed of monomeric lactate and glycolate units may comprise sequences of the type -L-G-

L-G- where L is a lactate unit and G is a glycolate unit. However, in a polymer formed of lactide and glycolide units, such a sequence would not be found unless rearrangement occurs, because the repeating units join the polymer as pairs of lactic and glycolic units. Thus, sequences such as -L-L-G-G- or -L-L-L-L-G-G- would typify a polymer formed of the lactide and glycolide units, and could by chance also be found in a polymer formed of the monomeric lactate and glycolate units. In a polymer formed of the dimeric units, each type of repeating unit would substantially always comprise a pair of identical monomeric units. Thus, one would not expect to find sequences of the -L-G-L-G- type. Due to this potential ambiguity, it is important to differentiate these two types of polymers.

The term "poly(lactide-glycolide)" "poly(lactide-co-glycolide)" or "PLG" may be used herein to refer solely to a copolymer or a copolymer segment formed of the dimeric repeating units, wherein the dimeric lactide and dimeric glycolide units make up the polymeric chain. A "poly (lactide-glycolide)" is typically formed through polymerization of the cyclic dimers lactide and glycolide, although it could also be theoretically formed through any process wherein dimeric units are incorporated in a given step of the polymerization process. The terms "polylactide" and "PL" refer to a polymer or a polymer segment wherein only lactide repeating units are present. Polylactide exists in two stereo forms, signified by a D or L for dexorotary or levorotary, or by DL for the racemic mix, e.g., poly(D, L-lactide) or poly(D, L-lactide-co-glycolide).

As used herein, the terms "poly(lactic acid-glycolic acid)", "poly(lactic acid-co-glycolic acid)", "poly(lactate-glycolate)", "poly(lactate-co-glycolate)", or "PLGA" may be used to refer solely to a polymer formed of the monomeric repeating units, wherein monomeric lactate and glycolate units make up the polymeric chain. A poly(lactic acid-glycolic acid) is formed by polymerization of monomeric lactic acid and monomeric glycolic acid or derivatives of those acids such as lower alkyl esters. Analogously, the terms "polylactate", "poly(lactic acid)" and "PLA" refer to polymer or polymer segments wherein only lactate repeating units are present. They are formed by polymerization of lactate. Poly(lactic acid) exists in two stereo forms, signified by a D or L for dexorotary or levorotary, or by DL for the racemic mix, e.g., poly(D,L-lactic acid) or poly(D,L-lactic acid-co-glycolic acid).

In some embodiments of the invention, the biodegradable polymer of the invention may comprise the polymeric segments selected from poly(lactide-co-glycolide) (PLG) copolymer, poly(lactic acid-co-glycolic acid) (PLGA) copolymer, or a combination thereof, wherein the ratio of monomeric lactide or lactic acid to glycolide or glycolic acid may be about 45:55 to about 99:1. In some instances, the biodegradable polymer of the invention comprises the polymeric segments selected from poly(lactide-co-glycolide) (PLG) copolymer, poly(lactic acid-co-glycolic acid) (PLGA) copolymer, or a combination thereof, wherein the ratio of monomeric lactide or lactic acid to glycolide or glycolic acid may be about 85:15. For instance, the polymer may comprise a PLG copolymeric segment composed of about 85:15 weight ratio of DL-lactide to glycolide. Similarly, the polymer may comprise a PLGA polymeric segment composed of about 85:15 weight ratio of DL-lactic acid to glycolic acid. The polymer may comprise combination of PLG and PLGA copolymeric segments, each composed of about 85:15 weight ratio of DL-lactide to glycolide or D,L-lactic acid to glycolic acid, respectively.

In some embodiments of the invention, about 100 mg, about 105 mg, about 110 mg, about 115 mg, about 120 mg, about 125 mg, about 130 mg, about 135 mg, about 140 mg, about 145 mg, 150 mg, about 155 mg, about 160 mg, about 165 mg, about 170 mg, about 175 mg, about 180 mg, about 185 mg, about 190 mg, about 195, or about 200 mg of the biodegradable polymer may be used in the extended release composition. In some instances, about 165 mg of the biodegradable polymer may be used in the extended release composition. In some embodiments of the invention, the amount of biodegradable polymer used in the extended release composition may represent about 40%, about 41%, about 42%, about 43%, about 44%, about 45%, about 46%, about 47%, about 48%, about 49%, or about 50% of the extended release composition based w:w. In some instances, the extended release composition comprises about 44% w:w of biodegradable polymer.

The term "number average molecular weight" may refer to the standard polymer parameter defined as the total weight of a sample divided by the total number of polymer molecules in the sample:

$$Mn=\Sigma iNiMi\Sigma iNi$$

where Ni is the number of molecules of molecular weight Mi.

The term "weight average molecular weight" may refer to the standard polymer parameter defined as:

$$Mw=\Sigma iNiMi2\Sigma iNiMi$$

where Ni is the number of molecules of molecular weight Mi.

In some embodiments, the biodegradable polymer may comprise a weight average molecular weight of about 6 kDa to about 45 kDa. In some further embodiments, the biodegradable polymer of the invention may comprise a weight average molecular weight of about 20 kDa, about 21 kDa, about 22 kDa, about 23 kDa, about 24 kDa, about 25 kDa, or about 26 kDa. It is to be understood that the two L/G copolymer segments need not be identical, and likely are not identical, either in sequence or in the molecular weight of each copolymer segment in a given polymer molecule. Furthermore, the specific composition of each molecule within a sample of the polymer varies in the same manner. The weight percent, and thus mole percent, of lactide or glycolide repeating monomeric units in the polymer can be varied by altering the weight percentages of the two reactants present in the polymerization reaction mixture.

The term "titratable carboxylic acid group", as used herein, may be used to refer to a carboxylic acid group in free form, that is, not bound as an ester or other derivative, wherein the carboxylic acid group can bear a free proton which may dissociate (ionize) in aqueous solution to form a carboxylate anion and a proton (acid). Therefore, an organic polymer with no titratable carboxylic acid groups is not an acidic polymer, and all carboxylate moieties within the polymer are bonded into esters, amides, or other non-acidic derivatives.

The absence of titratable carboxylic acid groups in the polymer of the invention means that the chemical functionality present on the terminal ends of the polymer, that is, on the groups at the distal ends of the copolymer segments linked to the core unit, are chemically neutral. As used herein, the term "chemically neutral" is defined as the absence of any polymer end groups, which are acidic or alkaline in nature and are therefore not ionizable in aqueous solution at around neutral pH. Chemical neutrality of a polymer is advantageous in that no acidic groups are present in the polymer to bring about auto-catalytic degradation through hydrolysis of the ester bonds of the polymer, or to catalyze degradation of a contained medicament, such as the peptide analog leuprolide, or to react with the contained medicament, such as with the amine groups on the peptide analog leuprolide.

Therefore, in some embodiments, the polymer of the extended release composition comprises a chemically neutral characteristic which helps prevent auto-catalytic degradation of the bonds adjoining the polymer segments to the core unit, as well preventing catalytic degradation of the contained GnRH or GnRH agonist (i.e. leuprolide acetate) of the extended release composition. Chemical neutrality of the polymer used herein is advantageous in maintaining the effective treatment of CPP in a child of at least 2 years of age for at least 6 months after a single dose of the composition, through the continuous extended release of leuprolide or a pharmaceutically acceptable equivalent thereof from the in situ depot. Furthermore, the biodegradable extended release composition, when administered into the body of a child of at least 2 years of age with CPP, displays no associated toxicity over a period of at least 6 months or longer as it is degraded in vivo.

In some embodiments of the invention, the biodegradable polymer is substantially insoluble in water and may be subsequently formulated in a biocompatible organic solvent, as previously defined, in order to prepare the extended release composition of the present invention for use in treating a child of at least 2 years of age with CPP. In some embodiments, the insoluble biodegradable polymer may be dissolved or suspended within a biocompatible organic solvent, such as NMP. In some instances, the dissolved or suspended polymer-organic solvent mixture may then be used to suspend an amount of GnRH or a GnRH agonist, such as leuprolide acetate. Alternatively, in another instance, the biodegradable polymer may be dissolved or suspended in a biocompatible organic solvent already containing an amount of GnRH or a GnRH agonist, such as leuprolide acetate. Combination of the biodegradable polymer with the biocompatible organic solvent and the GnRH or GnRH agonist yields the final extended release composition of the invention.

Stimulation Composition Parts

In some embodiments of the invention, the extended release composition used herein for the effective treatment of CPP within a child of at least 2 years of age may be used in a combined protocol with the administration of one or more stimulation compositions. Stimulation compositions, as further detailed below, are useful in measuring the peak blood serum concentration of one or more gonadotropins and/or sex hormones from a blood sample obtained from an individual after stimulation. Comprising GnRH or a GnRH agonist, such as leuprolide acetate for instance, stimulation compositions, when injected subcutaneously, stimulate the activation of gonadotropin receptors upon the cell surface of gonadotropic cells located within the anterior pituitary region of the brain. The following signal activation activates the pulsatile release of gonadotropins, LH and FSH, which subsequently trigger downstream release of sex hormones, such as testosterone and estradiol, from peripheral sex tissues (i.e. the testes and ovaries). Peak stimulated blood serum concentration levels of gonadotropins and/or sex hormones, as determined by use of a stimulation composition, can be medically useful in the diagnosis and/or monitoring of the progression of CPP, as well as monitoring the therapeutic response to a particular therapy or treatment option. In some instances, use of a stimulation composition may be used to determine the absence, presence, and/or extent of hypogonadism within an individual of interest, such as a child being treated for CPP.

As used herein, the term "peak stimulated blood serum concentration" may be defined as the blood serum concentration of any CPP-associated hormone including, but not limited to, LH, FSH, testosterone, or estradiol measured from a blood sample obtained within about 0.5 hours, about 0.75 hours, about 1.0 hours, about 1.25 hours, about 1.5 hours, about 1.75 hours, about 2.0 hours, about 2.25 hours, about 2.5 hours, about 2.75 hours, about 3 hours, or longer from a child after the administration of a stimulation test composition. Blood samples obtained from the child are then subjected to standard laboratory testing to measure the concentration of one or more CPP-associated hormones, such as LH, FSH, testosterone, or estradiol. In some embodiments of the invention, the peak stimulated blood serum concentration may be obtained before or after the administration of an extended release composition. A peak stimulated blood serum concentration obtained prior to administration of the extended release composition may also be termed as a "baseline peak stimulated blood serum concentration".

The term "non-peak blood serum concentration", as used herein, may be defined as the blood serum concentration of any CPP-associated hormone including, but not limited to, LH, FSH, testosterone, or estradiol measured from a blood sample obtained from a child in the absence of the administration of a stimulation test composition. In some embodiments of the invention, the non-peak blood serum concentration may be obtained before or after the administration of an extended release composition. A non-peak blood serum concentration obtained prior to administration of the extended release composition may also be termed as a "baseline non-peak blood serum concentration" or a "basal blood serum concentration". In some embodiments of the invention, the baseline non-peak blood serum concentration may be used for diagnostic purposes in screening a child suspected of having CPP. As non-peak blood serum concentrations do not depend upon the administration of a stimulation composition, blood samples may, generally, be obtained from a child at any time point before or after administration of the extended release composition. However, non-peak blood serum concentrations obtained from blood samples obtained from a child immediately (i.e. approximately within about 6 hours or less) after administration of the extended release composition may indicate a transient surge in LH and FSH concentrations due to the administration of the extended release composition. Obtained blood samples are then subjected to standard laboratory testing to measure the concentration of one or more CPP-associated hormones, such as LH, FSH, testosterone, or estradiol.

In some embodiments, the stimulation composition may comprises GnRH or at least one GnRH agonist or pharmaceutically equivalent or salt thereof selected from a group consisting essentially of leuprolide (leuprorelin), gonadorelin, goserelin, histrelin, nafarelin, buserelin, and triptorelin.

In some embodiments, the stimulation composition may comprise GnRH or a GnRH agonist dissolved or suspended as a liquid solution within one or more sterile containers (i.e. vial), which is ready for immediate administration. In some instances, the GnRH or GnRH agonist may be stored within a sterile container as a dried, lyophilized powder, which is then dissolved or suspended as a liquid solution prior to administration. In some embodiments, a single dose of the stimulation composition may be prepared as a liquid solution of about 10 μg to about 1000 μg in about 100 μL to about 2000 μL of water suitable for injection. For example, 1000 μg of leuprolide acetate may be prepared in about 200 μL water and used for subcutaneous injection within a child with CPP. In some instances, the prepared stimulation composition may be prepared as a single or as a multi-dose liquid solution for subcutaneous injection into a child with CPP. In some instances, GnRH or a GnRH agonist may be dissolved or suspended in a buffer of choice, such as, but not limited, sterile water suitable for injection.

In some instances, the stimulation composition may comprise a GnRH solution administered subcutaneously at a dose of about 100 μg total. Alternatively, in some instances, the stimulation composition may comprise a GnRH solution administered subcutaneously at a dose of about 2.5 μg per kg of the child's body weight. In some instances, the stimulation composition may comprise a leuprolide acetate solution administered subcutaneously at a dose of about 500 μg to about 1000 μg total. Alternatively, in some instances, the stimulation composition may comprise a leuprolide acetate solution administered subcutaneously at a dose of about 10 μg to about 20 μg per kg of the child's body weight. In some instances, the stimulation composition may comprise a nafarelin acetate solution administered subcutaneously at a dose of about 100 μg total. Alternatively, in some instances, the stimulation composition may comprise a nafarelin acetate solution administered subcutaneously at a dose of about 1 μg per kg of the child's body weight. In some instances, the stimulation composition may comprise a buserelin solution administered subcutaneously at a dose of about 100 μg total. In some instances, the stimulation composition may comprise a triptorelin acetate solution administered subcutaneously at a dose of about 100 μg total.

In some embodiments, a stimulation composition may be used for the initial diagnosis of CPP within a child of at least 2 years of age before the administration of an extended release composition according to the invention, as disclosed herein, for the treatment of CPP thereof. In other embodiments, a stimulation composition may be used to monitor the continued diagnosis of CPP within a child of at least 2 years of age after the administration of any one or more extended release composition(s) according to the invention, as disclosed herein, for the treatment of CPP thereof. In other embodiments, a stimulation composition may be used to monitor the progress or efficacy of treatment of CPP within a child of at least 2 years of age after the administration of any one or more extended release composition(s) according to the invention, as disclosed herein. Peak stimulated blood serum concentrations of LH of >5 IU/L at about thirty minutes post GnRH agonist stimulation can be considered to be diagnostic for CPP.

In some instances, the stimulation composition may be administered subcutaneously to a child in need thereof for measuring the peak stimulated blood serum concentration of one or more CPP-associated hormones. In some instances, the stimulation composition may administered subcutaneously to a child in need thereof for measuring the peak stimulated blood serum LH concentration. In some instances, the stimulation composition may administered subcutaneously to a child in need thereof for measuring peak stimulated blood serum FSH concentration. In some instances, the stimulation composition may administered subcutaneously to a male child in need thereof for measuring the peak stimulated blood serum testosterone concentration. In some instances, the stimulation composition may administered subcutaneously to a female child in need thereof for measuring the peak stimulated blood serum estradiol concentration.

Administration of Extended Release Composition for CPP

As disclosed herein, the extended release composition of the present invention comprises a biocompatible organic solvent, a GnRH agonist, and a biodegradable polymer with no substantially titratable carboxylic ends and at least one distal hydroxyl terminated end group, which is useful in an effective method of treating of CPP in a pediatric patient 2 years of age or older by administration once per about 6 months (or about 24 weeks). When subcutaneously injected into a child of at least 2 years of age having CPP, the extended release composition forms an in situ depot comprising the water insoluble biodegradable polymer and GnRH agonist as a coagulated or precipitated solid state mass through the dissipation or diffusion of the biocompatible organic solvent away from the injection site of the extended release composition and into surrounding host tissues. In some embodiments, the biodegradable polymer is composed of polymer segments selected from 85:15 poly(lactide-co-glycolide) (PLG) copolymer segments, 85:15 poly(lactic acid-co-glycolic acid) (PLGA) copolymer segments, or a combination thereof. In some embodiments, the biodegradable polymer is composed of polylactide (PL) or poly(lactic acid) (PLA) polymer segments, or a combination thereof. In some embodiments, the GnRH agonist is a leuprolide or a pharmaceutically acceptable equivalent thereof, including, but not limited to, leuprolide acetate. In one embodiment, the extended release composition is administered as a 45 mg (of leuprolide acetated) single subcutaneous injection once every six months. In some embodiments, the biocompatible organic solvent is NMP. In some embodiments, the extended release composition of the present invention is useful in the treatment of CPP in a pediatric patient 2 years of age or older by establishing hypogonadism via modulation of the Hypothalamic-Pituitary-Gonadal axis. In some embodiments, the extended release composition establishes hypogonadism for the effective treatment of CPP in a child through the suppression of gonadotropins, such as LH or FSH, and/or sex hormones, such as testosterone or estradiol.

In some embodiments, prior to initiation of treatment, a clinical diagnosis of CPP should be confirmed by measurement of serum concentrations of luteinizing hormone (LH) (basal or stimulated with a GnRH agonist), sex steroids, and assessment of bone age versus chronological age. In some instances, baseline evaluations may include height and weight measurements, diagnostic imaging of the brain (to rule out intracranial tumor), pelvic/testicular/adrenal ultrasound (to rule out steroid secreting tumors), human chorionic gonadotropin levels (to rule out a chorionic gonadotropin secreting tumor), and adrenal steroid measurements to exclude congenital adrenal hyperplasia. Measurement of serum concentrations of LH using a stimulation test with a GnRH agonist has been described in detail above.

In some embodiments, the extended release composition of the invention should be administered by a health care professional. In some instances, as with other drugs administered by subcutaneous injection, the injection site may need to be varied periodically. In some embodiments, the specific injection location chosen should be an area with sufficient soft or loose subcutaneous tissue, avoiding areas with brawny or fibrous subcutaneous tissue or locations that could be rubbed or compressed (i.e., by a belt or clothing waistband).

As used herein, the term "luteinizing hormone (LH)" may refer to a gonadotropic hormone comprising a heterodimeric glycoprotein encoded by the genes CGA and LHB and may be used interchangeably used with, but not limited to, "lutrophin", "lutropin", or "interstitial cell-stimulating hormone (ICSH) in males". LH plays a vital role in regulating testosterone production in males by stimulating Leydig cells in the testes. In females, LH is responsible for regulating ovulation, maintenance of corpus luteum, and secretion of estrogens, such as estradiol, through stimulation of Theca cells in the ovaries. Activity of LH is synergistic with FSH activity. Stimulation of testosterone and/or estradiol support a negative feedback loop by suppressing GnRH release, which thereby suppresses LH release. Prior to normal pubertal development, LH concentrations within a child are typically very low. However, LH levels >5 IU/L in a child younger in age than that typically associated with the normal onset of puberty (i.e. 8 or 9 years old in females and males, respectively) may be considered diagnostic for the presence of CPP within the child.

The term "follicle stimulating hormone (FSH)", as used herein, may be defined as a gonadotropic hormone comprising a heterodimeric glycoprotein encoded by the genes CGA and FSHB. FSH stimulates production of androgen-binding proteins, which enable onset of spermatogenesis. In females, FSH stimulates maturation of ovarian follicles within the ovaries. Activity of FSH is synergistic with LH activity. Prior to normal pubertal development, FSH concentrations within a child are typically very low. However, FSH levels >2.5 IU/L in a child younger in age than that typically associated with the normal onset of puberty (i.e. <10 or <9 years old in females and males, respectively) may be considered diagnostic for the presence of CPP within the child.

The term "gonadotropin receptors" may include, but are not limited to, "luteinizing hormone receptor (LHR)" and "follicle-stimulating hormone receptor (FSHR)". As noted previously, LHR should not be confused with LHRHR (i.e. GNRHR). LHR and FSHR are encoded by the LHCGR gene and FSHR gene, respectively. The sequence of LHR, FSHR, or any other gonadotropin receptor are readily known and available. Gonadotropin receptors, such as LHR and FSHR, are transmembrane receptors are located predominantly within ovarian, testes, and/or uterine tissues and are coupled to G-proteins for signal transduction. Activation of gonadotropin receptors is critical for stimulating sex hormone production and release. LHR and FSHR may be regulated by various gonadotropins and/or sex hormones through mechanisms including, but not limited to, 1) Upregulation, 2) Desensitization, 3) Downregulation, and/or 4) Modulation.

As used herein, the term "sex hormones" may refer to steroidal hormones that bind to androgen or estrogen receptors. Sex hormones may be used synonymously with, but not limited to, "sex steroids" or "peripheral sex steroids". Sex hormones are categorized into three broad types: 1) Progestogens, 2) Androgens, and 3) Estrogens. Progestogens include, but are not limited to, progesterone (P4) which plays a critical role in pregnancy and embryogenesis. Androgens include, but are not limited to, testosterone, which acts as the primary sex hormone in male sexual development. Estrogens include, but are not limited to, estradiol (E2), which acts as the primary sex hormone in female sexual development. It is to be noted, that although LH and FSH are generally not regarded to be sex hormones, there may be instances wherein the term "sex hormones" may be construed as implying LH and FSH. Release of testosterone and estradiol are critical for development and maturity of secondary sexual characteristics that occur during puberty in various physiological tissues, and are therefore tightly regulated. Sex hormones have multiple intracellular binding receptors that help regulate tissue specific responses to increased sex hormone concentrations. Furthermore, release of sex hormones can have additional activating or inhibiting properties on various tissues within the hypothalamic-pituitary-gonadal axis. For instance, both androgens and estrogens contribute to a negative feedback loop to decrease GnRH and gonadotropin production and release within the hypothalamus and pituitary of males and females, respectively.

In some instances, the extended release composition upon administration may release an initial amount of GnRH or GnRH agonist in a 'burst' phase as the extended release composition undergoes partial or complete solidification into an in situ depot. In some instances, the 'burst' phase may occur within about 6 hours or less upon administration. In some instances, the 'burst' phase may cause a temporary increase in a child's peak stimulated and/or non-peak blood serum concentration of gonadotropins, such as LH or FSH, and/or sex hormones, such testosterone or estradiol. In other embodiments, the 'burst' phase is followed by a 'plateau' phase wherein release of GnRH or a GnRH agonist is maintained at a continuous level in the blood. Continuous release of GnRH or a GnRH agonist from the in situ depot formed as a result of administering the extended release composition into a child of at least 2 years of age provides for the reduction of the child's peak stimulated and/or non-peak blood serum concentration of gonadotropins over time, such as LH or FSH, and/or sex hormones, such testosterone or estradiol. The peak stimulated blood serum concentration of gonadotropins and/or sex hormones may be measured from a blood sample obtained within about 0.5 hours, about 0.75 hours, about 1.0 hours, about 1.25 hours, about 1.5 hours, about 1.75 hours, about 2.0 hours, about 2.25 hours, about 2.5 hours, about 2.75 hours, about 3 hours, about 4 hours, about 5 hours, about 6 hours, or longer from a child after the administration of a stimulation test composition, wherein administration of the stimulation composition may occur before or at any time after the administration of the extended release composition. In some cases, the peak stimulated blood serum concentration of gonadotropins and/or sex hormones may be measured from a blood sample obtained from a child within as little as 30 minutes after administration of a stimulation composition.

The reduction of a child's peak stimulated blood serum concentration of gonadotropins and/or sex hormones upon administration of the extended release composition about once per 6 months (or about once per 24 weeks) provides for the effective therapeutic treatment of CPP within said child for a period of about 6 months (or about 24 weeks). Reduction of gonadotropins, such as LH or FSH, and/or sex hormones, such testosterone or estradiol, is useful in establishing hypogonadism within an individual, which is medically useful in the effective treatment of CPP in pediatric patients 2 years of age and older. Establishment of hypogonadism via suppression of gonadotropins and/or sex hormones is capable of slowing and/or halting development or advancement of secondary sexual characteristic associated with pubertal development. Inducing hypogonadism for a period of about 6 months (or about 24 weeks) or longer after a single dose is an advantageous property of the extended release composition of the invention as compared to shorter-acting treatment options, such as LUPRON DEPOT-PED® 1-month and 3-month, thereby yielding improved patient compliance. Conversely, the smaller injection dose volume of 0.375 mL and easier and less painful subcutaneous route of administration of the extended release composition are advantageous over similar and/or longer lasting treatment options, such as TRIPTODUR® and SUPPRELIN LA®.

In some embodiments, the response to the extended release composition upon subcutaneous administration may be monitored with a GnRH agonist stimulation test, basal serum LH levels, or serum concentration of sex steroid levels at about 3 to about 6 months following initiation of therapy and further as judged clinically appropriate, to confirm adequate suppression of pituitary gonadotropins, sex steroids, and progression of secondary sexual characteristics. Additionally, in some instances, height (for calculation of growth velocity) and bone age may be assessed at about every 6 to about every 12 months.

In some embodiments, the extended release composition reduces the peak stimulated blood serum concentration of LH to a pre-pubertal level of about <4 IU/L. In some instances, the extended release composition reduces the peak stimulated blood serum concentration of LH to a pre-pubertal level of about <4 IU/L by about 3 months (or about 12 weeks) or longer after administration of the first dose of the extended release composition. In some instances, administration of the extended release composition can reduce the peak stimulated blood serum concentration of LH to a level of about <4 IU/L for more than about 50%, more than about 55%, more than about 60%, more than about 65%, more than about 70%, more than about 75%, more than about 80%, more than about 85%, more than about 90%, more than about 95% or about 100% of children treated with the extended release composition at about 3 months (or 12 weeks) or longer following administration of the first dose. In some instances, the extended release composition reduces the peak stimulated blood serum concentration of LH to a pre-pubertal level of about <4 IU/L by about 6 months (or 24 weeks) or longer after administration of the first dose of the extended release composition. In some instances, administration of the extended release composition can reduce the peak stimulated blood serum concentration of LH to a level of about <4 IU/L for more than about 50%, more than about 55%, more than about 60%, more than about 65%, more than about 70%, more than about 75%, more than about 80%, more than about 85%, more than about 90%, more than about 95% or about 100% of children treated with the extended release composition at about 6 months or longer following administration of the first dose.

However, in some embodiments, if the peak stimulated blood serum concentration is about 4 IU/L or greater following administration of the stimulation composition at about 3 months (or about 12 weeks) or at about 6 months (or about 24 weeks) after administering the first dose of the extended release composition, then treatment of the child with CPP using the extended release composition may be discontinued. Cases where the peak stimulated blood serum concentration is about 4 IU/L or greater, at about 3 months (or 12 about 12 weeks) or at about 6 months (or about 24 weeks) after administering the first dose of the extended release composition, may be viewed as a child who is non-responsive to the extended release composition. As a non-limiting example, non-responsiveness to treatment may be an indicator of a potential misdiagnosis of CPP, and the child should therefore be re-evaluated for other more effective therapeutic approaches besides the extended release composition of the invention herein.

In some embodiments, the extended release composition reduces the peak stimulated blood serum concentration of FSH to a level of about 2.5 IU/L. In some instances, the extended release composition reduces the peak stimulated blood serum concentration of FSH to a level of about 2.5 IU/L at about 3 months (or about 12 weeks) after administration of the first dose of the extended release composition. In some instances, administration of the extended release composition can reduce the peak stimulated blood serum concentration of FSH to a level of about IU/L for more than about 50%, more than about 55%, more than about 60%, more than about 65%, more than about 70%, more than about 75%, more than about 80%, more than about 85%, more than about 90%, more than about 95% or about 100% of children treated with the extended release composition at about 3 months (or 12 weeks) or longer following administration of the first dose. In some instances, the extended release composition reduces the peak stimulated blood serum concentration of FSH to a level of about IU/L at about 6 months (or 24 weeks) after administration of the first dose of the extended release composition. In some instances, administration of the extended release composition can reduce the peak stimulated blood serum concentration of FSH to a level of about IU/L for more than about 50%, more than about 55%, more than about 60%, more than about 65%, more than about 70%, more than about 75%, more than about 80%, more than about 85%, more than about 90%, more than about 95% or about 100% of children treated with the extended release composition at about 6 months (or 24 weeks) or longer following administration of the first dose.

In some embodiments, the extended release composition reduces the peak stimulated blood serum concentration of estradiol in a female child to a level of about <73.4 pmol/L (i.e. 20 pg/mL; physicians within the U.S.A. generally use the 'pg/mL' unit notation for estradiol concentration). In some instances, the extended release composition reduces the peak stimulated blood serum concentration of estradiol in a female child to a level of about <73.4 pmol/L at about 3 months (or about 12 weeks) after administration of the first dose of the extended release composition. In some instances, administration of the extended release composition can reduce the peak stimulated blood serum concentration of estradiol to a level of about <73.4 pmol/L for more than about 50%, more than about 55%, more than about 60%, more than about 65%, more than about 70%, more than about 75%, more than about 80%, more than about 85%, more than about 90%, more than about 95% or about 100% of female children treated with the extended release composition at about 3 months (or about 12 weeks) or longer following administration of the first dose. In some instances, the extended release composition reduces the peak stimulated serum concentration of estradiol in a female child to a level of about <73.4 pmol/L at about 6 months (or about 24 weeks) after administration of the first dose of the extended release composition. In some instances, administration of the extended release composition can reduce the peak stimulated blood serum concentration of estradiol to a level of about <73.4 pmol/L for more than about 50%, more than about 55%, more than about 60%, more than about 65%, more than about 70%, more than about 75%, more than about 80%, more than about 85%, more than about 90%, more than about 95% or about 100% of female children treated with the extended release composition at about 6 months (or about 24 weeks) longer following administration of the first dose.

In some embodiments, the extended release composition reduces the peak stimulated blood serum concentration of testosterone in a male child to a level of about <1.0 nmol/L (i.e. approx. 28.8 ng/dL; physicians within the U.S.A. generally use the 'ng/dL' unit notation for testosterone concentration). In some instances, the extended release composition reduces the peak stimulated blood serum concentration of testosterone in a male child to a level of about <1.0 nmol/L at about 3 months (or about 12 weeks) after administration of the first dose of the extended release composition. In some instances, administration of the extended release composition can reduce the peak stimulated blood serum concentration of testosterone to a level of about <1.0 nmol/L for more than about 50%, more than about 55%, more than about 60%, more than about 65%, more than about 70%, more than about 75%, more than about 80%, more than about 85%, more than about 90%, more than about 95% or about 100% of male children treated with the extended release composition at about 3 months (or about 12 weeks) or longer following administration of the first dose. In some instances, the extended release composition reduces the peak stimulated blood serum concentration of testosterone in a male child to a level of about <1.0 nmol/L at about 6 months (or about 24 weeks) after administration of the first dose of the extended release composition. In some instances, administration of the extended release composition can reduce the peak stimulated blood serum concentration of testosterone to a level of about <1.0 nmol/L for more than about 50%, more than about 55%, more than about 60%, more than about 65%, more than about 70%, more than about 75%, more than about 80%, more than about 85%, more than about 90%, more than about 95% or about 100% of male children treated with the extended release composition at about 6 months (or about 24 weeks) or longer following administration of the first dose.

In some embodiments, the extended release composition may be effective for the treatment of CPP within a child of at least 2 years of age by reducing the development, advancement, or severity of at least one or more secondary sexual characteristics. In some instances, the secondary sexual characteristic may include, but are not limited to, bone growth velocity, growth age, Tanner stage, height, or weight.

In some instances, the extended release composition may reduce the growth velocity of a child up to about 25% over about a 12-month (or about 48 weeks) period comprising an initial administration of an extended release composition and a second administration of the extended release composition about 6 months (or about 24 weeks) after the first. However, reduction of growth velocity is influenced by the patient population and therefore, the extended release composition may be capable of reducing the bone growth velocity of any given CPP patient population by about more than 0%, about more than 5%, about more than 10%, about more than 15%, about more than 20%, about more than 25%, about more than 30%, about more than 35%, about more than 40%, about more than 45%, or about more than 50%. In some instances, the extended release composition may reduce the mean growth velocity of a child to about 9 cm or less per year at about 4 weeks and to about 7 cm or less per year after start of treatment. In other instances, the extended release composition may decrease the growth velocity of a child at about 3 months (or about 12 weeks), about 6 months (or about 24 weeks), or longer after administration from their growth velocity at about 1 month or about) 4 weeks after administration in more than about 50% of children treated with the extended release composition.

The term "dose" may be used to indicate a dose of the extended release composition, the stimulation composition, or both, administered to the "child" (pediatric patient) subcutaneously. In some embodiments, the injection dose volume of the extended release composition may be about 0.25 mL to about 0.5 mL per each administration. In some instances, injection dose volume of the extended release composition may be about 0.375 mL per each administration. The smaller injection dose volume of the extended release composition of the instant invention, which is delivered subcutaneously, is advantageous over other approved and marketed CPP treatment options which use much larger injection volumes delivered via more difficult and more painful routes of administration; for example, TRIPTODUR® uses a 2 mL dose volume administered through deep intramuscular injection into a child.

As used herein, the term "dosing regimen" may be used to indicate the subcutaneous administration of at least one dose of an extended release composition once about every six months to a child with CPP (i.e., a pediatric patient 2 years and older with CPP) in need of treatment thereof, with optional administration of at least one dose of a stimulation composition at defined time-points. In some embodiments, the optional stimulation composition may be administered at least once before administration of the extended release composition for measurement of peak stimulated blood serum concentration (i.e. baseline peak stimulated) of one or more CPP-associated hormones. In other embodiments, the optional stimulation composition may be administered at least once at about 3 months (or about 12 weeks) to about 6 months (or about 24 weeks) after administering the extended release composition for measurement of peak stimulated blood serum concentration of one or more CPP-associated hormones. In other embodiments, the optional stimulation composition may be administered at least once before administration of the extended release composition for measurement of peak-stimulated blood serum concentration (i.e. baseline peak stimulated) of one or more CPP-associated hormones and then may be administered at least once at about 3 months (or about 12 weeks) to about 6 months (or about 24 weeks) after administering the extended release composition for measurement of peak stimulated blood serum concentration of one or more CPP-associated hormones. In other embodiments, a dosing regimen may comprise enough doses of the extended release composition and enough doses of the optional stimulation composition to complete one treatment cycle of about 6 months (or about 24 weeks), two treatment cycles of about 12 months (or about 48 weeks), three treatment cycles of about 18 months (or about 72 weeks), four treatment cycles of about 24 months (or about 96 weeks), or more, as needed to effectively treat the pediatric patient with CPP in need thereof. For instance, by way of a non-limiting example, a 6, 12, 18, and 24-month dosing regimen could comprise 1, 2, 3, or 4 doses of the extended release composition, respectively, along with sufficient doses of the stimulation composition necessary for effective monitoring of the extended release composition's efficacy.

In some embodiments, a child's peak stimulated blood serum concentration of LH may be reduced or suppressed to a pre-pubertal level of about <4 IU/L over a period of about 6 months (or about 24 weeks) or longer by the administration of one or more dosing regimens comprising one or more doses of the extended release composition, where one or more doses of the optional stimulation composition are incorporated into the dosing regimen to confirm the initial diagnosis of CPP and/or to monitor the treatment of the child with the extended release composition. By way of a non-limiting example, in some instances, a dosing regimen useful for the effective treatment of CPP in a child of at least 2 years of age by reducing the child's peak stimulated blood serum concentration of LH to a pre-pubertal level of about <4 IU/L, may comprise an initial dose of the extended release composition followed by one or more subsequent doses of the extended release composition administered once about every 6 months (or about 24 weeks) after the previous dose until the child no longer is in need of effective CPP treatment. Efficacy of the extended release composition in effectively treating the child with CPP may be monitored via measuring the peak stimulated blood serum concentration level of LH in the child in response to administering one or more stimulation composition dose(s) at a time period of about 3 (or about 12 weeks) to about 6 months (or about 24 weeks) after administering each proceeding administered dose of the extended release composition.

Extended Release Composition and Stimulation Composition Kit

In addition to the method of using the extended release composition and stimulation composition for the effective treatment of pediatric patients 2 years of age and older with CPP, the present invention discloses a kit comprising at least one dose of the extended release composition, at least one dose of the stimulation composition, and instructions for the use thereof by a physician or other healthcare professional in treating said pediatric patients. In some embodiments, the kit contains at least one dose of the extended release composition within one or more sterile pre-filled, pre-packaged single-syringe or two-syringe system. In some embodiments, the kit contains at least one dose of the stimulation composition within one or more sterile pre-filled, pre-packaged syringe(s) or vial(s). In some embodiments, the kit may further include, but not limited solely to, additional needles, syringes, vials, alcohol swabs, blood sample collection vials, tourniquets, bandages/dressings, and/or labels in sufficient quantities as needed for a physician's or other healthcare professionals use when treating a child with CPP. In some instances, the needles used within the kit may be safety needles.

In some embodiments, the kit may contain the extended release composition within at least one single-syringe system, wherein it could be a single-compartment syringe, a two-compartment syringe, or other type of mixing syringe. In some embodiments, the single-syringe system may be pre-packaged with an effective amount of biocompatible organic solvent, leuprolide or a pharmaceutically acceptable equivalent or salt thereof, and biodegradable polymer for producing an extended release composition of the invention as described herein. In some instances, the single-syringe of the kit may contain an effective amount of NMP for producing an extended release composition of the invention as described herein. In some instances, the single-syringe of the kit may contain about 165 mg of NMP for producing an extended release composition of the invention as described herein. In some instances, the single-syringe of the kit may contain an effective amount of leuprolide or a pharmaceutically acceptable equivalent or salt thereof for producing an extended release composition of the invention as described herein. In some instances, the single-syringe of the kit may contain about 45 mg of leuprolide acetate. In some instances, the single-syringe of the kit may contain an amount of a pharmaceutically acceptable salt of leuprolide that provides 42 mg leuprolide free-base equivalent. In some instances, the single-syringe of the kit may contain an effective amount of a biodegradable polymer comprising a polymer segments selected from 85:15 poly(lactide-co-glycolide) (PLG) copolymer segments, 85:15 poly(lactic acid-co-glycolic acid) (PLGA) copolymer segments, or a combination thereof, wherein the polymer has substantially no titratable carboxylic acid groups and wherein at least one distal end group of the polymer is hydroxyl-terminated for producing an extended release composition of the invention as described herein. In some instances, the single-syringe of the kit may contain about 165 mg of a biodegradable polymer comprising a polymer segments selected from 85:15 poly(lactide-co-glycolide) (PLG) copolymer segments, 85:15 poly(lactic acid-co-glycolic acid) (PLGA) copolymer segments, or a combination thereof, wherein the polymer has substantially no titratable carboxylic acid groups and wherein at least one distal end group of the polymer is hydroxyl-terminated. In some instances, the single-syringe of the kit may contain an effective amount of a biodegradable polymer comprising a polymer segments selected from poly(lactide) (PL) polymer segments, poly (lactic acid) (PLA) polymer segments, or a combination thereof, wherein the polymer has substantially no titratable carboxylic acid groups and wherein at least one distal end group of the polymer is hydroxyl-terminated for producing an extended release composition of the invention as described herein.

In some embodiments, the kit may contain the extended release composition within at least one two-syringe system. In some embodiments, the two-syringe system comprises a first and a second syringe which may be interconnected via a slip-tip or luer-lock type connector, wherein connection forms a passageway in which a flowable liquid may be transferred from the first syringe into the second syringe or vice versa.

In some embodiments, the first syringe of the two-syringe system of the kit may be pre-packaged with effective amounts of biocompatible organic solvent and the biodegradable polymer of the invention, wherein the biodegradable polymer is dissolved within the biocompatible organic solvent for producing an extended release composition of the invention as described herein. In some instances, the first syringe of the two-syringe system of the kit may contain an effective amount of NMP necessary to dissolve a given amount of biodegradable polymer. In some instances, the first syringe of the two-syringe system of the kit may contain about 165 mg of NMP. In some instances, the first syringe of the two-syringe system of the kit may contain an effective amount of a biodegradable polymer comprising a polymer segments selected from 85:15 poly(lactide-co-glycolide) (PLG) copolymer segments, 85:15 poly(lactic acid-co-glycolic acid) (PLGA) copolymer segments, poly(lactide) (PL) polymer segments, poly(lactic acid) (PLA) polymer segments, or a combination thereof, wherein the polymer has substantially no titratable carboxylic acid groups and wherein at least one distal end group of the polymer is hydroxyl-terminated. In some instances, the first syringe of the two-syringe system of the kit may contain about 165 mg of a biodegradable polymer comprising a polymer segments selected from 85:15 poly(lactide-co-glycolide) (PLG) copolymer segments, 85:15 poly(lactic acid-co-glycolic acid) (PLGA) copolymer segments, poly(lactide) (PL) polymer segments, poly(lactic acid) (PLA) polymer segments, or a combination thereof, wherein the polymer has substantially no titratable carboxylic acid groups and wherein at least one distal end group of the polymer is hydroxyl-terminated. In some instances, the second syringe of the two-syringe system of the kit may contain an effective amount of leuprolide acetate, wherein the leuprolide or a pharmaceutically acceptable equivalent or salt thereof, wherein it may be a dried lyophilized powder. In some instances, the second syringe of the two-syringe system of the kit may contain about 45 mg of leuprolide acetate, wherein it may be a dried lyophilized powder.

In some embodiments, the extended release composition of the invention as contained within the two-syringe system of the kit may prepared by a physician or other healthcare professional prior to administering to a pediatric patient (child) 2 years of age or older with CPP in need of treatment thereof. In some instances, the extended release composition of the invention as contained within the two-syringe system of the kit may prepared by a physician or other healthcare professional within 30 minutes prior to administering to a pediatric patient 2 years of age or older with CPP in need of treatment thereof.

In some embodiments, the extended release composition of the invention as contained within the two-syringe system of the kit may be prepared by a physician or other healthcare professional by connecting the first syringe to the second syringe and continuously passing the biocompatible organic solvent-biodegradable polymer mixture contained within the first syringe back and forth into the second syringe to re-suspend the leuprolide or pharmaceutically acceptable equivalent or salt thereof. In some instances, uniform resuspension of the leuprolide or pharmaceutically acceptable equivalent or salt thereof within the biocompatible organic solvent-biodegradable polymer mixture may be achieved by continuously passing the contents back and forth between the first and second syringe for about at least 30 seconds, for about at least 35 seconds, for about at least 40 seconds, for about at least 45 seconds, for about at least 50 seconds, for about at least 55 seconds, for about at least 60 seconds, for about at least 65 seconds, for about at least 70 seconds, for about at least 75 seconds, for about at least 80 seconds, for about at least 85 seconds, for about at least 90 seconds, or longer to ensure complete resuspension. It is to be understood that none of the illustrated examples are meant to be encompassing of all possible variations in which the extended release composition may be prepared and/or packaged within a kit.

In some embodiments, the kit may contain at least one dose of the stimulation composition within one or more sterile pre-filled, pre-packaged syringe(s) or vial(s). In some instances, the kit may contain one or more syringes and/or vials with an effective amount of GnRH or a GnRH agonist for producing an extended release composition, wherein the GnRH or GnRH agonist may be present as a dried, lyophilized powder or as a liquid resuspension or solution in any appropriate buffer (i.e. water suitable for injection). In some embodiments, the appropriate buffer may further comprise at least one preservative and at least one tonicity adjustment agent. In some instances, the preservative may include, but is not limited to, benzyl alcohol. In other instances, the tonicity adjustment agent may be, but is not limited to, NaCl.

In some instances, the kit may contain one or more syringes and/or vials with a sufficient amount of GnRH or a GnRH agonist for at least one or more doses. For example, by way of a non-limiting example, the kit may contain at least one vial containing an effective amount of GnRH or a GnRH agonist to be re-suspended as a single dose by a physician or other healthcare professional for use as a stimulation composition. In such an example, the kit further contains at least one secondary syringe and/or vial containing an effective amount of buffer as necessary. Similarly, as a further non-limiting example, the kit may contain at least one vial containing an effective amount of GnRH or a GnRH agonist to be re-suspended as multiple doses by a physician or other healthcare professional for use as a stimulation composition. In such an example, the kit further contains at least one secondary syringe and/or vial containing an effective amount of buffer as necessary. Alternatively, as yet another non-limiting example, the kit may contain one or more syringes and/or vials already pre-filled with at least one or more single or multiple-dose amounts of the GnRH or GnRH agonist re-suspended in an appropriate amount of buffer as necessary. As a non-limiting illustrative example, the kit may comprise a vial containing a sterile, multiple dose solution of leuprolide acetate. In this example, the multi-dose vial may contain about 14 mg of leuprolide acetate solution re-suspended in about 2.8 mL of suitable buffer. Approximately about 0.2 mL of this 5 mg/mL solution may be used per injection (i.e. a total of 1000 μg leuprolide acetate used per stimulation composition dose), thereby providing up to about 14 doses. In some embodiments, the appropriate buffer used may further comprise an amount of at least one preservative and an amount of at least one tonicity adjustment agent. In some instances, the preservative may include, but is not limited to, benzyl alcohol. In other instances, the tonicity adjustment agent may be, but is not limited to, NaCl. By way of a non-limiting sample, the kit may contain a vial of appropriate buffer for use in preparing a 5 mg/mL solution of leuprolide acetate, wherein the appropriate buffer comprises about 9 mg/mL of benzyl alcohol for use as a preservative and about 6.3 mg/mL of NaCl for maintaining solution tonicity. It is to be understood that none of the illustrated examples are meant to be encompassing of all possible variations in which the stimulation composition may be prepared and/or packaged within a kit.

In some instances, the kit may comprise enough doses of the stimulation composition as needed for any desired dosing regimen, wherein at least one or more stimulation compositions are used per each dose of the extended release composition contained within the kit, wherein the extended release composition may be contained within a single-syringe or two-syringe system. For example, by way of a non-limiting example, a kit for a 6-month (or about 24 weeks) dosing regimen may comprise 1, 2, 3, or more stimulation composition doses alongside a single extended release composition dose. Similarly, a kit for a 12-month (or about 48 weeks) dosing regimen may comprise 1, 2, 3, 4, 5, 6, or more stimulation composition doses alongside two extended release composition doses. Likewise, a kit for a 18-month (or about 72 weeks) dosing regimen may comprise 1, 2, 3, 4, 5, 6, 7, 8, 9, or more stimulation composition doses alongside three extended release composition doses. Lastly, a kit for a 24-month (or about 96 weeks) dosing regimen may comprise 1, 2, 3, 4, 5, 6, 7, 8, 9, 10, 11, 12, or more stimulation composition doses alongside four extended release composition doses.

In some cases, the pre-filled sterile container and/or syringes may contain multiple doses of the stimulation composition. For example, a sterile container containing 3 doses worth of dried, lyophilized leuprolide acetate powder may be contained with a kit for a 6-month (or about 12 weeks) dosing regimen consisting of an initial, 3-month (or about 12 weeks), and 6-month (or about 24 weeks) stimulation composition to be administered to a child. In such an example, the dried, lyophilized leuprolide acetate may be re-suspended as a liquid solution containing 3 doses for 3 separate injections, wherein the container and its contents are properly stored until needed for each subsequent administration. Alternatively, in another example, a kit for a 6-month dosing regimen may consist of 3 separate, sterile containers or syringes each individually filled a single stimulation composition dose ready for administration. It is to be understood that none of the illustrated examples are meant to be encompassing of all possible variations in which the stimulation composition may be prepared and/or packaged within a kit.

All publications, patents, and patent documents are incorporated by reference herein, as though individually incorporated by reference. The invention will now be illustrated with the following non-limiting examples.

EXAMPLES

Example 1—General Procedure for Preparation of Biodegradable Polymer

In a jacketed stainless steel polymerization vessel, appropriate amounts of lactide and glycolide are added and the vessel contents are placed under a nitrogen atmosphere. The temperature of the vessel is increased until the reagents melt. An appropriate amount of an alkanediol is then added, followed by addition of stannous octanoate catalyst. The vessel is then heated at about 135-145° C. under nitrogen atmosphere for about 3-4 hours with constant stirring. Then, to remove unreacted lactide and glycolide monomers, the vessel is evacuated and the monomers are vacuum distilled out of the polymerization mixture. The hot melt is then extruded into cooling pans. After cooling, the solid mass is cryo-ground to a fine powder and dried.

Example 2—Preparation and Administration of a Leuprolide Acetate Extended Release Composition An extended release composition for use as a subcutaneous in situ depot in a pediatric patient 2 years of age or older for use as an effective treatment for CPP was prepared using a biodegradable polymer as prepared in Example 1. Components of the extended release composition of the invention are detailed in Table 1 below:

TABLE 1

| Extended Release Composition Reconstituted Drug Product | | |
|---|---|---|
| Reconstituted Drug Product | Leuprolide acetate delivered | 45 mg |
| | Approximate leuprolide free base equivalent | 42 mg |
| | PLG polymer delivered | 165 mg |
| | NMP delivered | 165 mg |
| | Approximate administered formulation weight | 375 mg |
| | Approximate injection volume | 0.375 mL |

The extended release composition is comprised of 165 mg of 85:15 poly(D,L-lactide-co-glycolide) (PLG) copolymer segments dissolved in 165 mg of NMP organic solvent. The biodegradable polymer is polymerized using a 1,6-hexanediol core unit, and is therefore hydroxyl terminated at its distal ends and contains substantially no titratable carboxylic acid groups. The biodegradable polymer possesses a weight average molecular weight between 20 kDa to 26 kDa. This liquid polymer mixture was subsequently deposited into a first sterile syringe and was irradiated. In a second sterile syringe, 45 mg of freeze-dried lyophilized leuprolide acetate powder was deposited, representing approximately 42 mg of free leuprolide base.

30 minutes prior to subcutaneous injection, the first and second syringes were allowed to warm to room temperature and then assembled via a luer-lock type connector into an interconnected 2-syringe apparatus. The liquid polymer mixture of the first syringe was then passed back and forth into the second syringe for at least 45 seconds at room temperature by a physician or other healthcare professional until all of the leuprolide acetate powder was re-suspended into a uniform suspension. The final volume of the prepared mixture was 0.375 mL with sufficient fluidity to be passed through a 5/8 inch 18 gauge syringe needle as a flowable extended release composition. Within 30 minutes of mixing the liquid polymer with the leuprolide acetate powder, the prepared dose was subcutaneously injected into a child previously diagnosed with CPP.

Example 3—A 12 Month Clinical Study for Treating Children with CPP

A multi-center, open-label, single arm, adaptive design was conducted to evaluate the efficacy and safety of the extended release composition described in Example 2 in treating pediatric patients 2 years of age or older with CPP. 114 male and female children suspected of having CPP, but who had not yet ever been treated with GnRH agonist based therapies, were administered a subcutaneous injection of a stimulation composition consisting of leuprolide acetate solution at a dose of either 20 μg/kg or 500 μg total depending on physician discretion, in order to confirm an initial diagnosis of CPP. Of the 114 subjects enrolled and screened, 50 children did not receive any dose of the extended release composition as they failed to meet additional screening criteria beyond confirmed CPP diagnosis and where therefore excluded from the instant clinical trial. The mean age was 7.5 years (range 4-9 years) at the start of treatment. Additional clinical markers for positive CPP diagnosis included children possessing a Tanner Stage 2 or 3 status (i.e. breast development in females or testicular volume 4 mL in males respectively) and/or a bone age to chronological age difference of year. Additionally, height and weight were also measured and evaluated.

All 64 subjects were then entered into a 12-month dosing regimen consisting of 2 doses of the extended release composition described in Example 2. Following CPP diagnostic confirmation via a stimulation test composition as described above, children were subcutaneously injected with a first dose of the extended release composition. Preferred injection sides included any region of subcutaneous tissue lacking excessive pigmentation, nodules, lesions, or hair, such as a child's abdomen or upper buttocks. Care was used to avoid using previously used injection sites. 64 children were treated with at least one dose of the extended release composition. At about 6 months after the first injection dose of the extended release composition, a second equal dose was administered to 60 subjects (four subjects received the first dose only). Importantly, neither doses of the extended release composition were altered at any time. All children, regardless of sex, age, size, ethnicity, duration of treatment, or severity of CPP diagnosis were treated with the exact same dosage.

At 3, 6, 9, and 12 months after the initial start of treatment with the first dose of the extended release composition, children were assessed for treatment efficacy, safety, and pharmacokinetics. Out of 64 study subjects, 4 had early termination of treatment, i.e. all subsequent administrations of either the extended release compositions for treatment and/or stimulation compositions for monitoring said treatment were terminated. Of the remaining 60 subjects, 58 were females and 2 were males. All remaining 60 children with CPP were naïve to previous GnRH agonist treatment with CPP and received two doses of the extended release composition and were observed for 12 months. The mean age was 7.5 years (range 4-9 years) at the start of treatment.

The pharmacokinetics of the extended release composition showed an initial burst release of leuprolide acetate peaking at 4 hours after the initial injection dose with a $C_{max}$ of 215.7 ng/mL with no apparent burst with any subsequently administered doses. The initial burst phase was followed by a plateau phase release of leuprolide acetate ranging from 0.18 ng/mL to 0.63 ng/mL from 4-weeks to 48-weeks with a mean of 0.37 ng/m L. Additional pharmacokinetic results are shown in Table 2 below:

TABLE 2

Mean Pharmacokinetic Parameters for Leuprolide in Subjects with CPP

| Extended Release | | Burst Phase (0-6 hrs) | | | Plateau Phase (4-48 weeks) |
|---|---|---|---|---|---|
| Composition | | $C_{max}$ | $T_{max}$ | AUC | AUC |
| Route | Dose | (ng/mL) | (hr) | (ng · hr/mL) | (ng · hr/mL) |
| SC | 45 mg | 215.7 | 3.7 | 953.7 | 9,592.5 |

As early as 3 months after the initial starting dose, the extended release composition was effective in reducing various CPP-associated hormones. The first dose of the extended release composition maintained suppression of these CPP-associated hormones continued up to 6-months. At 6-months after start of treatment, the second dose of the extended release composition was subcutaneously administered and was able to continue suppression of the CPP-associated hormones. Additionally, both the first and second doses were effective in slowing the growth velocity. The efficacy of the extended release composition in suppressing gonadotropins, sex hormones, and growth velocity in children with CPP is shown in Table 3 and Table 4 below as determined by immuno-based assays and/or high sensitivity Mass Spectrometry (LC-MS/MS):

TABLE 3

Efficacy of Extended Release Composition, 45 mg in Children with CPP

| | % (n/N) of Children Achieving Endpoints | | | |
|---|---|---|---|---|
| Endpoint | Month 3 | Month 6 | Month 9 | Month 12 |
| LH levels < 4 IU/L[1] | 84.7 (50/59) | 88.1 (52/59)[2] | 84.7 (50/59) | 84.7 (50/59) |
| Estradiol levels < 73.4 pmol/L (<20 pg/mL) | 98.2 (56/57) | 98.2 (56/57) | 98.2 (56/57) | 96.5 (55/57) |
| Testosterone levels < 1 nmol/L (<28.4 ng/dL) | 100.0 (2/2) | 100.0 (2/2) | 100.0 (2/2) | 50.0 (1/2) |
| FSH levels < 2.5 IU/L | 62.7 (37/59) | 69.5 (41/59) | 44.1 (26/59) | 54.2 (32/59) |
| Decrease in growth velocity from week 4 | 55.0 (33/60) | 52.5 (31/59) | 52.5 (31/59) | 51.7 (31/60) |

[1]Post GnRH agonist stimulation

[2]Primary Efficacy Endpoint

The suppression of gonadotropin and gonadal sex hormones (post GnRH agonist stimulation tests) and growth velocity during the study from screening to the end of study are shown in Table 4.

TABLE 4

Mean Values of Key Endpoints Over Time for Extended Release Composition, 4 mg in Children with CPP

| | Mean Value ± SD | | | | |
|---|---|---|---|---|---|
| Endpoint | Screening | Month 3 | Month 6 | Month 9 | Month 12 |
| LH levels (IU/L)[1] | 23.91 ± 24.56 | 3.11 ± 5.96 | 2.22 ± 2.05 | 2.26 ± 1.78 | 3.07 ± 6.17 |
| Estradiol levels[1] (pg/mL) | 26.01 ± 22.89 | 10.8 ± 4.51 | 10.4 ± 1.60 | 10.4 ± 1.57 | 10.7 ± 2.63 |
| Testosterone levels[1] (ng/dL) | 112.48 ± 69.34 | 15.86 ± 6.12 | 15.86 ± 6.12 | 11.54 ± 0.00 | 27.40 ± 22.43 |
| FSH levels (IU/L)[1] | 11.04 ± 8.09 | 2.78 ± 2.27 | 2.25 ± 1.62 | 3.05 ± 2.03 | 3.08 ± 2.27 |
| Growth Velocity (cm/year) | 8.54 ± 13.09[2] | 8.33 ± 4.82 | 6.92 ± 3.12 | 6.48 ± 2.27 | 6.29 ± 1.97 |

[1]Post GnRH agonist stimulation

[2]Calculated at week 4

Results showed that in children with CPP, the extended release composition reduced stimulated and basal gonadotropins to pre-pubertal levels. The extended release composition was effective in suppressing peak stimulated blood serum LH concentration to <4 IU/L in 88.1% of the study subjects by month 6. Nearly all subjects achieved suppression of estradiol or testosterone concentration to pre-pubertal levels at the 6-month assessment. Suppression was maintained throughout the study with the exception of 2 subjects (1 male and 1 female) at the 12-month assessment (see Table 3).

Additionally, over half of all study subjects experienced arrested or reversed progression of clinical signs of puberty with reductions in growth velocity and bone age. Mean growth velocity fell approximately 25%, from 8.54 cm/year at Week 4 to 6.29 cm/year at end of treatment. In the 6 months following the first dose, between Week 4 and Week 24, mean growth velocity decreased by approximately 19% to a mean growth velocity of 6.92 cm/year. In the 6 months following the second dose, between Week 24 and Week 48, the mean growth velocity was 5.79 cm/yr (SD=2.213), which represented an approximate 32% decrease from baseline. The mean ratio of bone age to chronological age at the time of measurement decreased by 4.9% from baseline to end of treatment.

Seven female subjects did not meet the primary efficacy criteria for LH<4 IU/L at 6 months. In four of the seven subjects, the LH level at 6 months was between 4.2 and 4.8 IU/L. The remaining three subjects had LH levels >5 IU/L. However, estradiol was suppressed to pre-pubertal levels in all seven subjects at each assessment.

In addition to effective suppression of CPP-associated hormones, the extended release composition effectively slowed or reversed secondary sexual characteristics within the children with CPP as seen in changes to their Tanner Stage status. Compared to baseline, males underwent a reversion from Tanner Stage 3 to Tanner Stage 2 after 12 months of treatment with regards to external genitalia development. After 12 months, approximately 55% of females underwent experienced at least or more downward shifts in their Tanner Stage assessment with regards to breast development. For both boys and girls, approximately 80% of the study subjects experienced no change in Tanner Stage status for public hair development after 12 months of treatment. Of the remaining, ⅓ underwent a decrease in status while the other ⅔ experienced an increase, both of which were shifts in direction of only 1 stage.

While various embodiments of the present invention have been described in detail, it is apparent that modifications and adaptations of those embodiments will occur to those skilled in the art. It is to be expressly understood, however, that such modifications and adaptations are within the scope of the present invention as set forth in the following claims.

The invention claimed is:

1. A method of treating central precocious puberty (CPP) in a pediatric patient 2 years of age or older having CPP, comprising the steps of:

(i) administering an initial dose of 45 mg leuprolide acetate to the pediatric patient 2 years of age or older with CPP by subcutaneous injection, wherein the leuprolide acetate is administered as a uniform suspension in an extended release composition comprising (a) a biodegradable polymer comprising polymers selected from 85:15 poly(lactic acid-co-glycolic acid) (PLGA) copolymers, 85:15 poly(lactide-co-glycolide) (PLG) copolymers, or a combination thereof, wherein the polymer has substantially no titratable carboxylic acid groups and at least one distal end group of the polymer is hydroxyl-terminated, and wherein the polymer is dissolved in (b) N-methyl-2-pyrrolidone (NMP), wherein the extended release composition delivers 45 mg leuprolide acetate in a 0.375 mL injection volume, wherein following administration into the pediatric patient the NMP dissipates out of the extended release formulation and an in situ solid depot is formed, wherein the in situ solid depot releases leuprolide acetate into the pediatric patient for a period of about 6 months, and wherein the dose of the leuprolide acetate is not individualized for the pediatric patient, (ii) monitoring the pediatric patient's response to the administration of the 45 mg leuprolide acetate by evaluating a GnRH agonist stimulation test, basal serum luteinizing hormone (LH) levels or serum concentration of sex steroid levels, in order to confirm suppression of pituitary gonadotropins, sex steroids, and progression of secondary sexual characteristics, and (iii) administering subsequent doses of the 45 mg leuprolide acetate composition described in (i) to the pediatric patient by subcutaneous injection once every 6 months until the patient achieves an age typically associated with the normal onset of puberty, wherein the release of leuprolide acetate from the in situ solid depot following administration of the initial and subsequent dose provides in a group of pediatric patients having a mean age of 7.5 years at the start of treatment an initial burst of release of leuprolide acetate after the first dose which peaks at 4 hours post dose administration with a mean maximum concentration of 215.7 ng/ml followed by a plateau phase extending from week 4 to week 48 wherein the release of leuprolide acetate is maintained at a continuous level ranging from 0.18 ng/ml to 0.63 ng/ml with a mean of 0.37 ng/mL.

2. The method of claim 1, wherein the method provides suppression of peak stimulated LH concentrations to less than 4 IU/L in more than about 80% of a group of pediatric patients after 12 months treatment.

3. The method of claim 2, wherein the method provides suppression of peak stimulated LH concentrations to less than 4 IU/L in approximately 85% of pediatric patients after 9 months treatment.

4. The method of claim 1, wherein the method provides suppression of estradiol levels to less than 20 μg/mL in more than about 95% of a group of pediatric female patients.

5. The method of claim 4, wherein the method provides suppression of estradiol levels to less than 20 μg/mL in approximately 98% of pediatric female patients after 9 months treatment.

6. The method of claim 1, wherein the method provides suppression of testosterone levels to less than 28.4 ng/dL in more than about 95% of a group of pediatric male patients.

7. The method of claim 1, further comprising the steps of assessing the pediatric patient's height for calculation of growth velocity every 3 to 6 months.

8. The method of claim 7, wherein the method provides a decrease in growth velocity over about a 9 month period of treatment in more than about 50% of pediatric patients after 12 months treatment.

9. The method of claim 8, wherein the method provides a decrease in growth velocity over about a 9 month period of treatment in more than about 50% of pediatric patients.

10. The method of claim 7, wherein the method provides a decrease in growth velocity up to about more than 20% over about a 9 month period of treatment.

11. The method of claim 7, wherein the method provides a decrease in mean growth velocity from about 9 cm or less per year at about 4 weeks to about 7 cm or less per year over about a 9 month period of treatment.

12. The method of claim 1, wherein following initial administration there is a temporary increase in the pediatric patient's blood serum concentration of gonadotropins and sex steroids.

13. The method of claim 1, wherein if the initial administration of the 45 mg dose of leuprolide acetate to the pediatric patient is insufficient to suppress pituitary gonadotropins, sex steroids and progression of secondary sexual characteristics as determined by evaluating a GnRH agonist stimulation test, basal serum luteinizing hormone (LH) levels or serum concentration of sex steroid levels, then treatment with the extended release formulation of leuprolide acetate is discontinued.

14. A method of treating central precocious puberty (CPP), comprising administering a dose of 45 mg leuprolide acetate to pediatric patients 2 years of age or older with CPP by subcutaneous injection, and continuing administration of the 45 mg leuprolide acetate to the pediatric patients by subcutaneous injection once every 6 months, wherein the leuprolide acetate is administered as a uniform suspension in an extended release composition comprising (a) a biodegradable polymer comprising polymers selected from 85:15 poly(lactic acid-co-glycolic acid) (PLGA) copolymers, 85:15 poly(lactide-co-glycolide) (PLG) copolymers, or a combination thereof, wherein the polymer has substantially no titratable carboxylic acid groups and at least one distal end group of the polymer is hydroxyl-terminated, and wherein the polymer is dissolved in (b) N-methyl-2-pyrrolidone (NMP), wherein the extended release composition delivers 45 mg leuprolide acetate in a 0.375 mL injection volume, wherein following administration into the pediatric patient the NMP dissipates out of the extended release formulation and an in situ solid depot is formed, wherein the in situ solid depot releases leuprolide acetate into the pediatric patient for a period of about 6 months and provides an initial burst phase of release of leuprolide acetate with a mean maximum serum leuprolide concentration in the range of 215.7 ng/ml which peaks at about 4 hours after the initial injection of the 45 mg leuprolide acetate dose followed by a plateau phase of release of the leuprolide acetate, wherein the serum leuprolide acetate concentration ranges from 0.18 ng/mL to 0.63 ng/ml from 4 weeks to 48 weeks with a mean of 0.37 ng/ml, and wherein the method provides a suppression of peak stimulated LH concentrations to less than 4 IU/L after 12 months treatment in more than 80% of pediatric patients being treated, based on evaluation in a group of pediatric patients having a mean age of 7.5 years at the start of treatment.

15. The method of claim 14, further comprising:

(i) monitoring the pediatric patient's response to the administration of the 45 mg leuprolide acetate by evaluating a GnRH agonist stimulation test, basal serum luteinizing hormone (LH) levels or serum concentration of sex steroid levels in order to confirm suppression of pituitary gonadotropins, sex steroids and progression of secondary sexual characteristics, and (ii) if suppression is confirmed, continuing administration of the 45 mg leuprolide acetate to the pediatric patient by subcutaneous injection once every 6 months until the patient achieves an age typically associated with the normal onset of puberty, and if suppression is not confirmed, discontinuing administration.

16. The method of claim 14, wherein the method further provides a decrease in growth velocity up to about more than 20% over about a 12 month period of treatment in more than about 50% of pediatric patients, based on evaluation in a group of pediatric patients having a mean age of 7.5 years at the start of treatment.

17. The method of claim 14, wherein the method provides suppression of estradiol levels to less than 20 μg/mL in approximately 95% or more of pediatric female patients after 12 months treatment, based on evaluation in a group of pediatric patients having a mean age of 7.5 years at the start of treatment.

18. The method of claim 14, wherein the method provides suppression of testosterone levels to less than 28.4 ng/dL in approximately 100% of pediatric male patients after 9 months treatment, based on evaluation in a group of pediatric patients having a mean age of 7.5 years at the start of treatment.

19. A method of treating central precocious puberty (CPP), comprising (i) administering a dose of 45 mg leuprolide acetate to pediatric patients 2 years of age or older with CPP by subcutaneous injection, and continuing administration of the 45 mg leuprolide acetate to the pediatric patients by subcutaneous injection once every 6 months, wherein the leuprolide acetate is administered as a uniform suspension in an extended release composition comprising (a) a biodegradable polymer comprising polymers selected from 85:15 poly(lactic acid-co-glycolic acid) (PLGA) copolymers, 85:15 poly(lactide-co-glycolide) (PLG) copolymer segments, or a combination thereof, wherein the polymer has substantially no titratable carboxylic acid groups and at least one distal end group of the polymer is hydroxyl-terminated, and wherein the polymer is dissolved in (b)N-methyl-2-pyrrolidone (NMP), wherein the extended release composition delivers 45 mg leuprolide acetate in a 0.375 mL injection volume, wherein following administration into the pediatric patient the NMP dissipates out of the extended release formulation and an in situ solid depot is formed, and wherein the in situ solid depot releases leuprolide acetate into the pediatric patient for a period of about 6 months, (ii) monitoring the pediatric patient's response to the administration of the 45 mg leuprolide acetate by evaluating a GnRH agonist stimulation test, basal serum luteinizing hormone (LH) levels or serum concentration of sex steroid levels in order to confirm suppression of pituitary gonadotropins, sex steroids and progression of secondary sexual characteristics, and (iii) if suppression is confirmed, continuing administration of the 45 mg leuprolide acetate to the pediatric patient by subcutaneous injection once every 6 months until the patient achieves an age typically associated with the normal onset of puberty, and if suppression is not confirmed, discontinuing administration, wherein the release of leuprolide acetate from the in situ solid depot following administration of an initial and subsequent dose provides in a group of pediatric patients having a mean age of 7.5 years at the start of treatment an initial burst of release of leuprolide acetate after the first dose which peaks at 4 hours post dose administration with a mean maximum serum leuprolide concentration of 215.7 ng/ml followed by a plateau phase extending from week 4 to week 48 wherein the release of leuprolide acetate is maintained at a continuous level ranging from 0.18 ng/ml to 0.63 ng/ml with a mean of 0.37 ng/ml, wherein the method provides (a) a suppression of peak stimulated LH concentrations to less than 4 IU/L after 12 months treatment in more than 80% of pediatric patients being treated, (b) a decrease in growth velocity up to about more than 20% over about a 12 month period of treatment in more than about 50% of pediatric patients, (c) a suppression of estradiol levels to less than 20 μg/mL in approximately 95% or more of pediatric female patients after 12 months treatment, and (d) a suppression of testosterone levels to less than 28.4 ng/dL in approximately 100% of pediatric male patients after 9 months treatment.

* * * * *